US006432702B1

(12) United States Patent
Basilico et al.

(10) Patent No.: US 6,432,702 B1
(45) Date of Patent: *Aug. 13, 2002

(54) MAMMALIAN GROWTH FACTOR NUCLEIC ACIDS, VECTORS, AND HOST CELLS

(75) Inventors: Claudio Basilico, New York, NY (US); Pasquale Delli Bovi, Portici (IT)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/478,486

(22) Filed: Jun. 7, 1995

Related U.S. Application Data

(60) Division of application No. 08/187,780, filed on Jan. 25, 1994, now Pat. No. 5,459,250, which is a continuation of application No. 07/901,705, filed on Jun. 22, 1992, now abandoned, which is a continuation-in-part of application No. 07/806,771, filed on Dec. 6, 1991, now abandoned, which is a continuation of application No. 07/177,506, filed on Apr. 4, 1988, now abandoned, which is a continuation-in-part of application No. 07/062,925, filed on Jun. 16, 1987, now abandoned.

(51) Int. Cl.[7] ......................... C12N 15/12; C12N 5/06; C12N 15/09; C12N 1/20
(52) U.S. Cl. ................. 435/325; 435/320.1; 435/252.3; 435/252.33; 435/357; 435/365; 536/23.5
(58) Field of Search .......................... 514/2, 12; 435/6, 435/62.1, 320.1, 325, 252.3, 357, 365, 252.33; 536/23.5

(56) References Cited

U.S. PATENT DOCUMENTS

| | | | |
|---|---|---|---|
| 4,444,760 A | | 4/1984 | Thomas |
| 4,716,102 A | | 12/1987 | Levy |
| 5,106,731 A | | 4/1992 | Salhudden et al. |
| 5,126,323 A | | 6/1992 | Rogers et al. |
| 5,352,589 A | * | 10/1994 | Bergonzoni et al. ........ 435/69.4 |
| 5,387,673 A | * | 2/1995 | Seddon et al. .............. 530/399 |
| 5,639,862 A | * | 6/1997 | Treada et al. ............... 530/399 |

FOREIGN PATENT DOCUMENTS

WO WO 8607595 12/1986

OTHER PUBLICATIONS

Moscatelli et al., *Fed. Proc.*, 45:6, 1382, 1986.
Abraham et al., *Science*, 233:545–548, 1986.
Gimenez–Gallego et al. *Biochem. Biophys. Res. Comm.*, 135:611–617, 1986.
Sakamoto et al., *Proc. Natl. Acad. Sci.*, 83:3997–4001, 1986.
Taira et al., *Proc. Natl. Acad. Sci.*, 84:2980–2984, 1987.
Rueger et al., *Antibiot. Chemother. (Basel)*, 32:43–7, 1984 (abstract only).
Boldogh et al., *Int. J. Cancer*, 28:469–474, 1981 (abstract only).
Abraham et al., *EMBO J.*, 5: 10, 2523–2528, 1986.
Esch et al., *Proc. Natl. Acad. Sci.*, 82:6507–6511, 1985.
Delli–Bovi et al., *Cell*, 50:729–735, 1987.
Delli–Bovi et al., *Proc. Natl. Acad. Sci.*, 84:5660–5664, 1987.
Delli–Bovi et al., *Mol. and Cell. Bio.*, 8:2933–2941, 1988.
Huebner et al., *Onc. Res.*, 3:263–270, 1988.
Quarto et al., *Onc. Res.*, 5:101–110, 1989.
Velcich et al., *Onc. Res.*, 5:31–37, 1989.
Basilico et al., *Annals of N.Y. Acad. Sci.*, 567:95–103, 1989.
Kaner et al., *Science*, 248:1410–1413, 1990.
Mansukhani et al., *Proc. Natl. Acad. Sci.*, 87:4222–4225, 1990.
Talarico et al., *Proc. Natl. Acad. Sci.*, 87:4222–4225, 1990.
Curatola et al., *Mol. and Cell. Bio.*, 10:2475–2484, 1990.
Talarico et al., *Mol. and Cell. Bio.*, 11:1138–1145, 1991.
Mansukhani et al., *Proc. Natl. Acad. Sci.*, 89:3305–3309, 1992.
Bernstein, S.C. et al., *PNAS* 82: 1726–1730, 1980.5.
Lo, S.C., et al., *AJP* 118:7–13, 1985.
Diamond, A. et al., *Nature* 305:112–116, Sep., 1983.
Diamond, A. et al., *Science* 225:516–519, Aug., 1984.
Garrity, R.R. et al., *Gene* 68:63–72.
Lerman, M.I. et al., *Int J. Cancer* 37: 293–302, 1986.
Colburn, N.H. et al., *Mol. & Cell. Biol.* 3:1182–1186, 1983.
Colburn, N.H. et al., *Cancer Research* 48:1195–1200, 1988.
181162w, *Chem. Abs.* 108, 1986.
164592z, *Chem. Abs.* 101, 1984.
4527g, *Chem. Abs.* 96, 1982.
147328h, *Chem. Abs.* 105, 1986.
Gallego et al., *Biochem & Biophys.* 135:2, 541–548, 1986.
Weiss et al., *Clin. Res.*, 34:2, 537A, 1986.
165184n, *Chem Abs.* 105, 1986.
192304z, *Chem Abs.* 107, 1987.
Abraham et al., *Science*, 223:545–548, Aug., 1986.

* cited by examiner

*Primary Examiner*—Marianne P. Allen
(74) *Attorney, Agent, or Firm*—Darby & Darby

(57) ABSTRACT

A truncated mammalian growth factor, displaying homology to both basic and acidic fibroblast growth factor in a single polypeptide, is disclosed herein. The growth factor is substantially smaller (i.e. has fewer amino acid residues) than the full-length mammalian growth factor, has a higher affinity for fibroblast growth factor receptors than full-length K-FGF and basic fibroblast growth factor and increased mitogenic activity. Also disclosed herein are DNA sequences encoding the truncated growth factor, pharmaceutical formulations containing the truncated growth factor and methods to heal burns and wounds in a mammal by administering the pharmaceutical formulations.

21 Claims, 12 Drawing Sheets

```
                                                       A
                                                       ↓
  1    MSGPGTAAVALLPAVLLALLAPWAGRGGAAAPTAPNGTLEAELERRWESL          50
       _____    ***
                                      ↑↑
 51    VALSLARLPVAAQPKE AAVQSGAGDYLLGIKRLRRLYCNVGIGFHLQALP         100

101    DGRIGGAHADTRDSLLELSPVERGVVSIFGVASRFFVAMSSKGKLYGSPF          150

151    FTDECTFKEILLPNNYNAYESYKYPGMFIALSKNGKTKKGNRVSPTMKVT          200

201    HFLPRL 206
```

FIG. 1

Probe G
A  1 2 3 4 5

←28S
←18S

Probe H
B  1 2 3 4 5

←28S
←18S

SEQUENCE LISTING

<160> NUMBER OF SEQ ID NOS: 14

<210> SEQ ID NO 1
<211> LENGTH: 140
<212> TYPE: PRT
<213> ORGANISM: Human

<400> SEQUENCE: 1

```
Ala Ala Val Gln Ser Gly Ala Gly Asp Tyr Leu Leu Gly Ile Lys Arg
  1               5                  10                  15

Leu Arg Arg Leu Tyr Cys Asn Val Gly Ile Gly Phe His Leu Gln Ala
             20                  25                  30

Leu Pro Asp Gly Arg Ile Gly Gly Ala His Ala Asp Thr Arg Asp Ser
         35                  40                  45

Leu Leu Glu Leu Ser Pro Val Glu Arg Gly Val Val Ser Ile Phe Gly
     50                  55                  60

Val Ala Ser Arg Phe Phe Val Ala Met Ser Ser Lys Gly Lys Leu Tyr
 65                  70                  75                  80
```

```
Gly Ser Pro Phe Phe Thr Asp Glu Cys Thr Phe Lys Glu Ile Leu Leu
                85                  90                  95

Pro Asn Asn Tyr Asn Ala Tyr Glu Ser Tyr Lys Tyr Pro Gly Met Phe
            100                 105                 110

Ile Ala Leu Ser Lys Asn Gly Lys Thr Lys Gly Asn Arg Val Ser
            115                 120                 125

Pro Thr Met Lys Val Thr His Phe Leu Pro Arg Leu
    130                 135                 140

<210> SEQ ID NO 2
<211> LENGTH: 423
<212> TYPE: DNA
<213> ORGANISM: Human

<400> SEQUENCE: 2
gcggccgtcc agagcggcgc cggcgactac ctgctgggca tcaagcggct gcggcggctc    60
tactgcaacg tgggcatcgg cttccacctc caggcgctcc ccgacggccg catcggcggc   120
gcgcacgcgg acacccgcga cagcctgctg gagctctcgc ccgtggagcg gggcgtggtg   180
agcatcttcg gcgtggccag ccggttcttc gtggccatga gcagcaaggg caagctctat   240
ggctcgccct tcttcaccga tgagtgcacg ttcaaggaga ttctccttcc caacaactac   300
aacgcctacg agtcctacaa gtaccccggc atgttcatcg ccctgagcaa gaatgggaag   360
accaagaagg ggaaccgagt gtcgcccacc atgaaggtca cccacttcct ccccaggctg   420
tga                                                                  423

<210> SEQ ID NO 3
<211> LENGTH: 145
<212> TYPE: PRT
<213> ORGANISM: Bos taurus

<400> SEQUENCE: 3

Pro Ala Leu Pro Glu Asp Gly Gly Ser Gly Ala Phe Pro Pro Gly His
 1               5                  10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Ser
            100                 105                 110

Ser Trp Tyr Val Ala Leu Lys Arg Thr Gly Gln Tyr Lys Leu Gly Pro
        115                 120                 125

Lys Thr Pro Gly Gln Lys Ala Ile Leu Phe Leu Pro Met Ser Ala Lys
    130                 135                 140

Ser
145

<210> SEQ ID NO 4
<211> LENGTH: 140
<212> TYPE: PRT
<213> ORGANISM: Bos taurus
```

<400> SEQUENCE: 4

```
Phe Asn Leu Pro Leu Gly Asn Tyr Lys Pro Lys Leu Leu Tyr Cys
  1               5                  10                  15
Ser Asn Gly Gly Tyr Phe Leu Arg Ile Leu Pro Asp Gly Thr Val Asp
             20                  25                  30
Gly Thr Lys Asp Arg Ser Asp Gln His Ile Gln Leu Gln Leu Cys Ala
             35                  40                  45
Glu Ser Ile Gly Glu Val Tyr Ile Lys Ser Thr Glu Thr Gly Gln Phe
 50                  55                  60
Leu Ala Met Asp Thr Asp Gly Leu Leu Tyr Gly Ser Gln Thr Pro Asn
 65                  70                  75                  80
Glu Glu Cys Leu Phe Leu Glu Arg Leu Glu Glu Asn His Tyr Asn Thr
                 85                  90                  95
Tyr Ile Ser Lys Lys His Ala Glu Lys His Trp Phe Val Gly Leu Lys
                100                 105                 110
Lys Asn Gly Arg Ser Lys Leu Gly Pro Arg Thr His Phe Gly Gln Lys
                115                 120                 125
Ala Ile Leu Phe Leu Pro Leu Pro Val Ser Ser Asp
        130                 135                 140
```

<210> SEQ ID NO 5
<211> LENGTH: 423
<212> TYPE: DNA
<213> ORGANISM: Human

<400> SEQUENCE: 5

```
gcggccgtcc agagcggcgc cggcgactac ctgctgggca tcaagcggct gcggcggctc    60
tactgcaacg tgggcatcgg cttccacctc caggcgctcc ccgacggccg catcggcggc   120
gcgcacgcgg acacccgcga cagcctgctg gagctctcgc ccgtggagcg gggcgtggtg   180
agcatcttcg gcgtggccag ccggttcttc gtggccatga gcagcaaggg caagctctat   240
ggctcgccct tcttcaccga tgagtgcacg ttcaaggaga ttctccttcc caacaactac   300
aacgcctacg agtcctacaa gtaccccggc atgttcatcg ccctgagcaa gaatgggaag   360
accaagaagg ggaaccgagt gtcgcccacc atgaaggtca cccacttcct ccccaggctg   420
tga                                                                423
```

<210> SEQ ID NO 6
<211> LENGTH: 27
<212> TYPE: DNA
<213> ORGANISM: Human

<400> SEQUENCE: 6

```
gcggccgtcc agagcggcgc cggcgac                                       27
```

<210> SEQ ID NO 7
<211> LENGTH: 30
<212> TYPE: DNA
<213> ORGANISM: Artificial Sequence
<220> FEATURE:
<223> OTHER INFORMATION: sequence produced from human K-FGF by
      site-directed mutagenesis

<400> SEQUENCE: 7

```
atggcagcag ttcaatcagg agcaggcgac                                    30
```

<210> SEQ ID NO 8

<211> LENGTH: 10
<212> TYPE: PRT
<213> ORGANISM: Artificial Sequence
<220> FEATURE:
<223> OTHER INFORMATION: sequence of human K-FGF (amino acids 67-75) modified to contain initiator methionine

<400> SEQUENCE: 8

Met Ala Ala Val Gln Ser Gly Ala Gly Asp
 1               5                  10

<210> SEQ ID NO 9
<211> LENGTH: 618
<212> TYPE: DNA
<213> ORGANISM: Human

<400> SEQUENCE: 9

| | | | | | |
|---|---|---|---|---|---|
| atgtcgggc | ccgggacggc | cgcggtagcg | ctgctcccgg | cggtcctgct | ggccttgctg | 60 |
| gcgccctggg | cgggccgagg | gggcgccgcc | gcacccactg | cacccaacgg | cacgctggag | 120 |
| gccgagctgg | agcgccgctg | ggagagcctg | gtggcgctct | cgttggcgcg | cctgccggtg | 180 |
| gcagcgcagc | ccaaggaggc | ggccgtccag | agcggcgccg | cgactacct | gctgggcatc | 240 |
| aagcggctgc | ggcggctcta | ctgcaacgtg | ggcatcggct | ccacctcca | ggcgctcccc | 300 |
| gacggccgca | tcgcggcgc | gcacgcggac | acccgcgaca | gcctgctgga | gctctcgccc | 360 |
| gtggagcggg | gcgtggtgag | catcttcggc | gtgccagcc | ggttcttcgt | ggccatgagc | 420 |
| agcaagggca | agctctatgg | ctcgcccttc | ttcaccgatg | agtgcacgtt | caaggagatt | 480 |
| ctccttccca | caactacaa | cgcctacgag | tcctacaagt | accccggcat | gttcatcgcc | 540 |
| ctgagcaaga | atgggaagac | caagaagggg | aaccgagtgt | cgcccaccat | gaaggtcacc | 600 |
| cacttcctcc | ccaggctg | | | | | 618 |

<210> SEQ ID NO 10
<211> LENGTH: 528
<212> TYPE: DNA
<213> ORGANISM: Human

<400> SEQUENCE: 10

| | | | | | |
|---|---|---|---|---|---|
| gcacccactg | cacccaacgg | cacgctggag | gccgagctgg | agcgccgctg | ggagagcctg | 60 |
| gtggcgctct | cgttggcgcg | cctgccggtg | gcagcgcagc | ccaaggaggc | ggccgtccag | 120 |
| agcggcgccg | cgactacct | gctgggcatc | aagcggctgc | ggcggctcta | ctgcaacgtg | 180 |
| ggcatcggct | ccacctcca | ggcgctcccc | gacggccgca | tcgcggcgc | gcacgcggac | 240 |
| acccgcgaca | gcctgctgga | gctctcgccc | gtggagcggg | gcgtggtgag | catcttcggc | 300 |
| gtgccagcc | ggttcttcgt | ggccatgagc | agcaagggca | agctctatgg | ctcgcccttc | 360 |
| ttcaccgatg | agtgcacgtt | caaggagatt | ctccttccca | caactacaa | cgcctacgag | 420 |
| tcctacaagt | accccggcat | gttcatcgcc | ctgagcaaga | atgggaagac | caagaagggg | 480 |
| aaccgagtgt | cgcccaccat | gaaggtcacc | cacttcctcc | ccaggctg | | 528 |

<210> SEQ ID NO 11
<211> LENGTH: 1142
<212> TYPE: DNA
<213> ORGANISM: Human

<400> SEQUENCE: 11

| | | | | | |
|---|---|---|---|---|---|
| ggcgcgcact | gctcctcaga | gtcccagctc | cagccgcgcg | ctttccgccc | ggctcgccgc | 60 |
| tccatgcagc | cggggtagag | cccggcgccc | ggggccccg | tcgcttgcct | cccgcacctc | 120 |

-continued

```
ctcggttgcg cactcccgcc cgaggtcggc cgtgcgctcc cgcgggacgc cacaggcgca      180
gctctgcccc ccagcttccc gggcgcactg accgcctgac cgacgcacgc cctcgggccg      240
ggatgtcggg gcccgggacg gccgcggtag cgctgctccc ggcggtcctg ctggccttgc      300
tggcgccctg ggcgggccga gggggcgccg ccgcacccac tgcacccaac ggcacgctgg      360
aggccgagct ggagcgccgc tgggagagcc tggtggcgct ctcgttggcg cgcctgccgg      420
tggcagcgca gcccaaggag gcggccgtcc agagcggcgc cggcgactac ctgctgggca      480
tcaagcggct gcggcggctc tactgcaacg tgggcatcgg cttccacctc caggcgctcc      540
ccgacggccg catcggcggc gcgcacgcgg acacccgcga cagcctgctg agctctcgc      600
ccgtggagcg gggcgtggtg agcatcttcg gcgtggccag ccggttcttc gtggccatga      660
gcagcaaggg caagctctat ggctcgccct tcttcaccga tgagtgcacg ttcaaggaga      720
ttctccttcc caacaactac aacgcctacg agtcctacaa gtaccccggc atgttcatcg      780
ccctgagcaa gaatgggaag accaagaagg ggaaccgagt gtcgcccacc atgaaggtca      840
cccacttcct ccccaggctg tgaccctcca gaggacccctt gcctcagcct cgggaagccc      900
ctgggagggc agtgcgaggg tcaccttggt gcactttctt cggatgaaga gtttaatgca      960
agagtaggtg taagatattt aaattaatta tttaaatgtg tatatattgc caccaaatta     1020
tttatagttc tgcgggtgtg ttttttaatt ttctgggggg aaaaaagac aaaacaaaaa     1080
accaactctg acttttctgg tgcaacagtg gagaatctta ccattggatt tctttaactt     1140
gt                                                                    1142
```

<210> SEQ ID NO 12
<211> LENGTH: 206
<212> TYPE: PRT
<213> ORGANISM: Human

<400> SEQUENCE: 12

```
Met Ser Gly Pro Gly Thr Ala Ala Val Ala Leu Leu Pro Ala Val Leu
 1               5                  10                  15
Leu Ala Leu Leu Ala Pro Trp Ala Gly Arg Gly Gly Ala Ala Ala Pro
             20                  25                  30
Thr Ala Pro Asn Gly Thr Leu Glu Ala Glu Leu Glu Arg Arg Trp Glu
         35                  40                  45
Ser Leu Val Ala Leu Ser Leu Ala Arg Leu Pro Val Ala Ala Gln Pro
     50                  55                  60
Lys Glu Ala Ala Val Gln Ser Gly Ala Gly Asp Tyr Leu Leu Gly Ile
 65                  70                  75                  80
Lys Arg Leu Arg Arg Leu Tyr Cys Asn Val Gly Ile Gly Phe His Leu
                 85                  90                  95
Gln Ala Leu Pro Asp Gly Arg Ile Gly Gly Ala His Ala Asp Thr Arg
            100                 105                 110
Asp Ser Leu Leu Glu Leu Ser Pro Val Glu Arg Gly Val Val Ser Ile
        115                 120                 125
Phe Gly Val Ala Ser Arg Phe Phe Val Ala Met Ser Ser Lys Gly Lys
    130                 135                 140
Leu Tyr Gly Ser Pro Phe Phe Thr Asp Glu Cys Thr Phe Lys Glu Ile
145                 150                 155                 160
Leu Leu Pro Asn Asn Tyr Asn Ala Tyr Glu Ser Tyr Lys Tyr Pro Gly
                165                 170                 175
Met Phe Ile Ala Leu Ser Lys Asn Gly Lys Thr Lys Lys Gly Asn Arg
```

```
              180                 185                 190
Val Ser Pro Thr Met Lys Val Thr His Phe Leu Pro Arg Leu
        195                 200                 205
```

<210> SEQ ID NO 13
<211> LENGTH: 176
<212> TYPE: PRT
<213> ORGANISM: Human

<400> SEQUENCE: 13

```
Ala Pro Thr Ala Pro Asn Gly Thr Leu Glu Ala Glu Leu Glu Arg Arg
 1               5                  10                  15
Trp Glu Ser Leu Val Ala Leu Ser Leu Ala Arg Leu Pro Val Ala Ala
                20                  25                  30
Gln Pro Lys Glu Ala Ala Val Gln Ser Gly Ala Gly Asp Tyr Leu Leu
            35                  40                  45
Gly Ile Lys Arg Leu Arg Arg Leu Tyr Cys Asn Val Gly Ile Gly Phe
        50                  55                  60
His Leu Gln Ala Leu Pro Asp Gly Arg Ile Gly Gly Ala His Ala Asp
 65                  70                  75                  80
Thr Arg Asp Ser Leu Leu Glu Leu Ser Pro Val Glu Arg Gly Val Val
                 85                  90                  95
Ser Ile Phe Gly Val Ala Ser Arg Phe Phe Val Ala Met Ser Ser Lys
            100                 105                 110
Gly Lys Leu Tyr Gly Ser Pro Phe Phe Thr Asp Glu Cys Thr Phe Lys
        115                 120                 125
Glu Ile Leu Leu Pro Asn Asn Tyr Asn Ala Tyr Glu Ser Tyr Lys Tyr
    130                 135                 140
Pro Gly Met Phe Ile Ala Leu Ser Lys Asn Gly Lys Thr Lys Lys Gly
145                 150                 155                 160
Asn Arg Val Ser Pro Thr Met Lys Val Thr His Phe Leu Pro Arg Leu
                165                 170                 175
```

<210> SEQ ID NO 14
<211> LENGTH: 175
<212> TYPE: PRT
<213> ORGANISM: Human

<400> SEQUENCE: 14

```
Pro Thr Ala Pro Asn Gly Thr Leu Glu Ala Glu Leu Glu Arg Arg Trp
 1               5                  10                  15
Glu Ser Leu Val Ala Leu Ser Leu Ala Arg Leu Pro Val Ala Ala Gln
                20                  25                  30
Pro Lys Glu Ala Ala Val Gln Ser Gly Ala Gly Asp Tyr Leu Leu Gly
            35                  40                  45
Ile Lys Arg Leu Arg Arg Leu Tyr Cys Asn Val Gly Ile Gly Phe His
        50                  55                  60
Leu Gln Ala Leu Pro Asp Gly Arg Ile Gly Gly Ala His Ala Asp Thr
 65                  70                  75                  80
Arg Asp Ser Leu Leu Glu Leu Ser Pro Val Glu Arg Gly Val Val Ser
                 85                  90                  95
Ile Phe Gly Val Ala Ser Arg Phe Phe Val Ala Met Ser Ser Lys Gly
            100                 105                 110
Lys Leu Tyr Gly Ser Pro Phe Phe Thr Asp Glu Cys Thr Phe Lys Glu
        115                 120                 125
Ile Leu Leu Pro Asn Asn Tyr Asn Ala Tyr Glu Ser Tyr Lys Tyr Pro
```

-continued

```
            130                 135                 140
Gly Met Phe Ile Ala Leu Ser Lys Asn Gly Lys Thr Lys Lys Gly Asn
145                 150                 155                 160

Arg Val Ser Pro Thr Met Lys Val Thr His Phe Leu Pro Arg Leu
                165                 170                 175
```

MAMMALIAN GROWTH FACTOR NUCLEIC ACIDS, VECTORS, AND HOST CELLS

This is a division of application Ser. No. 08/187,780, filed Jan. 25. 1994; now U.S. Pat. No. 5,459,250 which is a continuation of application Ser. No. 07/901,705, filed Jun. 22, 1992, now abandoned; which is a continuation-in-part of application Ser. No. 07/806,771, filed Dec. 6, 1991; now abandoned which is a continuation of application Ser. No. 07/177,506, filed Apr. 4, 1988; now abandoned which is a continuation-in-part of application Ser. No. 07/062,925, filed Jun. 16, 1987, now abandoned.

The United States Government has rights to this invention by virtue of grant No. CA42568 from The National Cancer Institute.

FIELD OF THE INVENTION

This invention pertains to a mammalian growth factor, pharmaceutical formulations comprising said factor and methods for healing wounds or burns in mammals comprising administering said formulations.

BACKGROUND OF THE INVENTION

This invention pertains to a novel polypeptide having mammalian growth factor activity and to methods for using it.

A variety of diffusible factors which stimulate the growth of cells in a hormone-like manner are generally called "growth factors". Growth factors are often present in serum and have also been isolated from a variety of organs. They are protein molecules (or groups of such molecules) and in all known cases they interact with specific cell surface receptors to promote cellular growth and/or differentiation. Growth factors vary in their tissue specificity, i.e. some interact only with specific cell types, while others are active on a wider cell type range.

Among the best known groups of mammalian growth factors are: (1) platelet derived growth factor (PDGF), released from platelets; (2) epidermal growth factor (EGF); (3) hematopoietic growth factors (including interleukins 1, 2, and 3), required for growth and differentiation of lymphocytes, and colony stimulating factors (CSF), promoting growth and differentiation of hematopoietic stem cells; (4) angiogenic (literally "blood-vessel-forming") growth factors, such as the fibroblast growth factors (FGF) believed to promote growth and organization of endothelial cells into new blood vessels; (5) miscellaneous growth factors released by tumor cells.

Two well-characterized angiogenic factors are basic and acidic fibroblast growth factors (FGF), believed to be most important in vivo for endothelial cell growth. However, neither basic FGF nor acidic FGF has proven useful as pharmaceutical agents for promotion of wound healing. Several factors may contribute to the unsuitability of basic FGF and acidic FGF as pharmaceutical agents. Neither factor is sufficiently stable for effective pharmaceutical formulation. Basic FGF demonstrates restricted interaction with FGF receptors in vitro, and thus cannot be expected to interact with all FGF receptors in vivo. Finally, basic FGF and acidic FGF have thus far proven ineffective in animal models.

Co-pending U.S. patent application Ser. No. 07/806,771 (abandoned) filed Dec. 6, 1991 discloses an angiogenic mammalian growth factor isolated from Kaposi's Sarcoma cells and having substantial homology to each of acidic and basic fibroblast growth factor in a single polypeptide. The growth factor protein comprises 176 amino acid residues and is a mature (secreted) glycoprotein. This growth factor has variously been called K-FGF or FGF-4, and it has shown promising results as a wound healing agent in preclinical studies in an ischemic rabbit ear model. In such a model, K-FGF promoted wound healing better than basic or acidic FGF.

Growth factors are believed to promote wound healing. For example, EGF present in saliva is believed to accelerate wound healing in mice. Schultz G. S et al. (*Science* 232:350–352, 1986) report that transforming growth factor (TGF)-alpha and vaccinia virus growth factor (VGF), both of which are substantially homologous to EGF, accelerated epidermal wound healing in pigs when topically applied to second degree burns and were significantly more active than EGF.

Of the above-mentioned growth factors, the angiogenic growth factors would be particularly useful as wound healing agents because of their ability to promote the formation and growth of new blood vessels.

OBJECTS OF THE INVENTION

It is an object of the present invention to provide a novel growth factor useful as a wound healing agent in mammals.

Another object of the present invention is to provide a mammalian growth factor with increased biologic activities.

Yet another object of the present invention is to provide novel pharmaceutical formulations and methods for promoting wound healing in mammals.

A still further object of the present invention is to provide a truncated mammalian growth factor protein having substantial homology to each of acidic and basic fibroblast growth factor protein in a single polypeptide and having substantially higher specific activity than K-FGF protein.

SUMMARY OF THE INVENTION

The present invention pertains to a previously unknown form of truncated mammalian growth factor protein having substantial homology to each of basic and acidic fibroblast growth factor proteins in a single polypeptide chain, said truncated mammalian growth factor being substantially smaller than the full-length mammalian growth factor (the truncated protein is hereinafter referred to as truncated K-FGF or K-FGF-140).

In another aspect, the present invention provides a polypeptide having the amino acid sequence (SEQ. ID. NO. 1):

```
Ala Ala Val Gln Ser Gly Ala Gly Asp Tyr Leu Leu Gly Ile Lys Arg
 1           5               10                  15
Leu Arg Arg Leu Tyr Cys Asn Val Gly Ile Gly Phe His Leu Gln Ala
            20              25                  30
Leu Pro Asp Gly Arg Ile Gly Gly Ala His Ala Asp Thr Arg Asp Ser
        35              40                  45
Leu Leu Glu Leu Ser Pro Val Glu Arg Gly Val Val Ser Ile Phe Gly
    50              55                  60
Val Ala Ser Arg Phe Phe Val Ala Met Ser Ser Lys Gly Lys Leu Tyr
 65             70                  75              80
Gly Ser Pro Phe Phe Thr Asp Glu Cys Thr Phe Lys Glu Ile Leu Leu
            85                  90                  95
Pro Asn Asn Tyr Asn Ala Tyr Glu Ser Tyr Lys Tyr Pro Gly Met Phe
            100             105                 110
Ile Ala Leu Ser Lys Asn Gly Lys Thr Lys Lys Gly Asn Arg Val Ser
        115             120                 125
Pro Thr Met Lys Val Thr His Phe Leu Pro Arg Leu.
    130                 135             140
```

In yet another aspect, the present invention provides a pharmaceutical formulation for treating a mammal suffering from wounds or burns comprising truncated K-FGF and a pharmaceutically acceptable carrier or diluent.

A still further aspect of the present invention involves a method for healing wounds or burns in a mammal in need of such treatment by administration of an effective amount for wound or burn healing of truncated K-FGF.

A still further aspect of the present invention provides an isolated DNA having the sequence (SEQ. ID. NO. 2):

```
GCG GCC GTC CAG AGC GGC GCC GGC GAC TAC CTG CTG GGC      39
ATC AAG CGG CTG CGG CGG CTC TAC TGC AAC GTG GGC ATC      78
GGC TTC CAC CTC CAG GCG CTC CCC GAC GGC CGC ATC GGC     117
GGC GCG CAC GCG GAC ACC CGC GAC AGC CTG CTG GAG CTC     156
TCG CCC GTG GAG CGG GGC GTG GTG AGC ATC TTC GGC GTG     195
GCC AGC CGG TTC TTC GTG GCC ATG AGC AGC AAG GGC AAG     234
CTC TAT GGC TCG CCC TTC TTC ACC GAT GAG TGC ACG TTC     273
AAG GAG ATT CTC CTT CCC AAC AAC TAC AAC GCC TAC GAG     312
TCC TAC AAG TAC CCC GGC ATG TTC ATC GCC CTG AGC AAG     351
AAT GGG AAG ACC AAG AAG GGG AAC CGA GTG TCG CCC ACC     390
ATG AAG GTC ACC CAC TTC CTC CCC AGG CTG TGA             423
```

A still further aspect of the present invention provides an isolated DNA comprising the sequence (SEQ ID NO:10):

```
333      340       350          360        370        380
 *        *         *            *          *          *
GCA CCC ACT GCA CCC AAC GGC ACG CTG GAG GCC GAG CTG GAG CGC CGC
Ala Pro Thr Ala Pro Asn Gly Thr Leu Glu Ala Glu Leu Glu Arg Arg 390       400        410        420
          *         *          *          *
TGG GAG AGC CTG GTG GCG CTC TCG TTG GCG CGC CTG CCG GTG GCA GCG
Trp Glu Ser Leu Val Ala Leu Ser Leu Ala Arg Leu Pro Val Ala Ala 430       440        450        460        470
 *         *          *          *          *
```

-continued

```
            CAG CCC AAG GAG GCG GCC GTC CAG AGC GGC GCC GGC GAC TAC CTG CTG
            Gln Pro Lys Glu Ala Ala Val Gln Ser Gly Ala Gly Asp Tyr Leu Leu 480         490         500         510         520
                 *           *           *           *           *
            GGC ATC AAG CGG CTG CGG CGG CTC TAC TGC AAC GTG GGC ATC GGC TTC
            CAC
            Gly Ile Lys Arg Leu Arg Arg Leu Tyr Cys Asn Val Gly Ile Gly Phe
            His 530         540         550         560         570
             *           *           *           *           *
            CTC CAG GCG CTC CCC GAC GGC CGC ATC GGC GGC GCG CAC GCG GAC ACC
            Leu Gln Ala Leu Pro Asp Gly Arg Ile Gly Gly Ala His Ala Asp Thr 580         590         600         610         620
                 *           *           *           *           *
            CGC GAC AGC CTG CTG GAG CTC TCG CCC GTG GAG CGG GGC GTG GTG AGC
            Arg Asp Ser Leu Leu Glu Leu Ser Pro Val Glu Arg Gly Val Val Ser 630         640         650         660         670
                     *           *           *           *           *
            ATC TTC GGC GTG GCC AGC CGG TTC TTC GTG GCC ATG AGC AGC AAG GGC
            Ile Phe Gly Val Ala Ser Arg Phe Phe Val Ala Met Ser Ser Lys Gly 680         690         700         710
                     *           *           *           *
            AAG CTC TAT GGC TCG CCC TTC TTC ACC GAT GAG TGC ACG TTC AAG GAG
            Lys Leu Tyr Gly Ser Pro Phe Phe Thr Asp Glu Cys Thr Phe Lys Glu 720         730         740         750         760
             *           *           *           *           *
            ATT CTC CTT CCC AAC AAC TAC AAC GCC TAC GAG TCC TAC AAG TAC CCC
            Ile Leu Leu Pro Asn Asn Tyr Asn Ala Tyr Glu Ser Tyr Lys Tyr Pro 770         780         790         800         810
             *           *           *           *           *
            GGC ATG TTC ATC GCC CTG AGC AAG AAT GGG AAG ACC AAG AAG GGG AAC
            Gly Met Phe Ile Ala Leu Ser Lys Asn Gly Lys Thr Lys Lys Gly Asn 820         830         840         850         860
                 *           *           *           *           *
            CGA GTG TCG CCC ACC ATG AAG GTC ACC CAC TTC CTC CCC AGG CTG
            Arg Val Ser Pro Thr Met Lys Val Thr His Phe Leu Pro Arg Leu-
```

A still further aspect of the present invention provides a truncated K-FGF protein characterized by (i) a molecular weight of about 14,000 Daltons;.and (ii) an average FGF-receptor binding affinity of about $9.5 \times 10^{-11}$M.

A still further aspect of the present invention provides an isolated DNA comprising the sequence (SEQ ID NO:9):

```
ATG TCG GGG CCC GGG ACG GCC GCG GTA GCG CTG CTC CCG GCG GTC

CTG CTG GCC TTG CTG GCG CCC TGG GCG GGC CGA GGG GGC GCC GCC

GCA CCC ACT GCA CCC AAC GGC ACG CTG GAG GCC GAG CTG GAG CGC

CGC TGG GAG AGC CTG GTG GCG CTC TCG TTG GCG CGC CTG CCG GTG

GCA GCG CAG CCC AAG GAG GCG GCC GTC CAG AGC GGC GCC GGC GAC

TAC CTG CTG GGC ATC AAG CGG CTG CGG CGG CTC TAC TGC AAC GTG

GGC ATC GGC TTC CAC CTC CAG GCG CTC CCC GAC GGC CGC ATC GGC

GGC GCG CAC GCG GAC ACC CGC GAC AGC CTG CTG GAG CTC TCG CCC

GTG GAG CGG GGC GTG GTG AGC ATC TTC GGC GTG GCC AGC CGG TTC

TTC GTG GCC ATG AGC AGC AAG GGC AAG CTC TAT GGC TCG CCC TTC

TTC ACC GAT GAG TGC ACG TTC AAG GAG ATT CTC CTT CCC AAC AAC

TAC AAC GCC TAC GAG TCC TAC AAG TAC CCC GGC ATG TTC ATC GCC
```

-continued

```
CTG AGC AAG AAT GGG AAG ACC AAG AAG GGQ AAC CGA GTG TCG CCC

ACC ATG AAG GTC ACC CAC TTC CIC CCC AGG CTG
```

These and other aspects of the present invention will be apparent to those of ordinary skill in the art in light of the present description, claims and drawings.

BRIEF DESCRIPTION OF THE DRAWINGS

FIG. 1 is a diagram depicting the amino acid sequence of the full-length K-FGF protein and the amino acid sequence of the truncated protein of the present invention, K-FGF-140.

DETAILED DESCRIPTION OF THE INVENTION

Figure 2:
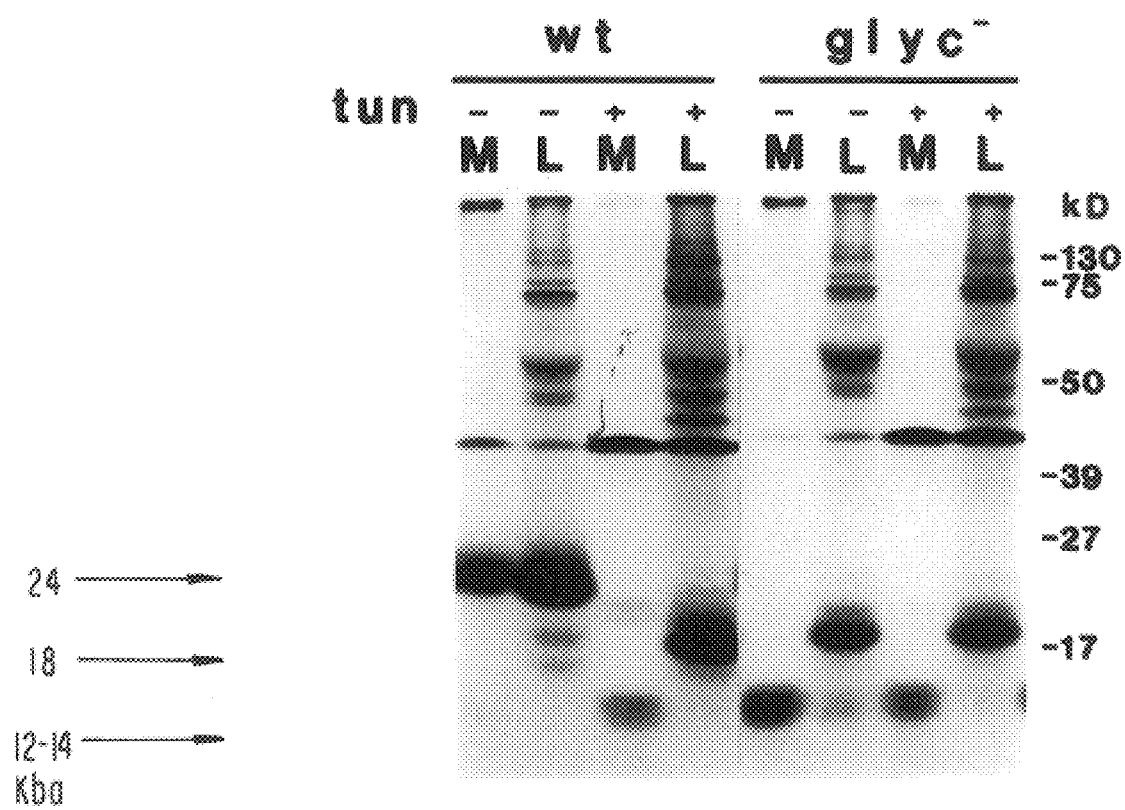
FIG. 2 is an autoadiograph of a sodium dodecyl sulfate polyacrylamide gel electrophoretic (SDS-PAGE) analysis of immunoprecipitated K-FGF forms produced in COS cells transfected with either wild type K-FGF or K-FGF-140 DNA or with a mutated K-FGF cDNA which expresses an unglycosylated form of K-FGF that is processed to produce K-FGF-140.

All patent applications, patents and literature references mentioned in the specification are incorporated by reference in their entirety. In the case of inconsistencies, the present disclosure, including definitions, shall prevail.

The present inventors have surprisingly found a truncated form of the K-FGF protein which demonstrates substantially increased activity over that of either full-length K-FGF, basic FGF, or acidic FGF. The truncated K-FGF protein is not glycosylated and is substantially smaller (i.e. has fewer amino acid residues) than the full-length K-FGF protein. The truncated protein has a higher affinity for fibroblast growth factor receptors than either the mature, full-length K-FGF protein or bFGF. In addition, the truncated protein has a higher affinity for heparin than full-length K-FGF and increased mitogenic (i.e. growth promoting) activity. It is expected that, due to these increased biological activities, the truncated protein of the present invention will also have increased wound healing activity.

"Substantially smaller" refers to the fact that the truncated K-FGF protein of the invention contains about 140 amino acid residues as contrasted with the 176 amino acid residues that are present in the full-length mature, secreted K-FGF protein.

"K-FGF-140" is defined herein as the unglycosylated, truncated mammalian growth factor protein of the present invention.

"K-FGF" is defined herein as the full-length mature human growth factor having a molecular weight of about 18,000 Daltons (non-glycosylated) comprising 1.76 amino acid residues as disclosed in U.S. patent application Ser. No. 07/806,771 (abandoned) filed Dec. 6, 1991.

"Mitogenic activity" in reference to the biological activity of the truncated protein of the present invention is defined herein as the ability of the protein to induce DNA synthesis and proliferation of cells in culture.

"Substantial homology to each of acidic and basic fibroblast growth factors" is defined herein as having regions of identity (either exact or by conservative substitution) to said growth factors as shown in Table 1 below.

K-FGF-140 was discovered during studies on the effect of glycosylation on the secretion of full-length K-FGF. Simian COS cells that were transfected with a plasmid encoding the full-length human K-FGF protein and incubated with tunicamycin (an inhibitor of N-linked glycosylation), accumulated an unglycosylated K-FGF protein within the cells of approximately 18,000 Daltons (the expected size of the unglycosylated full-length K-FGF protein). Surprisingly, only proteins of 12,000–14,000 Daltons were detected in the culture medium (i.e. were secreted). This was more clearly shown using a K-FGF cDNA mutated in such a way to express a protein in which amino acid 38 (Threonine) of the full length K-FGF,precursor protein was replaced by Alanine. This protein cannot be glycosylated. COS cells transfected with a plasmid encoding this mutated form of K-FGF also accumulate within the cells an unglycosylated K-FGF protein of approximately 18,000 daltons, but produce in the medium only forms of 12,000–14,000 daltons. Apparently the removal of the sugar residues exposes sites on the K-FGF molecule that are very susceptible to cleavage by cellular proteases located on the cell surface. Thus the protein is cleaved to produce these smaller forms as soon as it becomes externalized. It has been determined that the 14,000 Dalton species is K-FGF-140, a truncated form of the full-length K-FGF protein.

K-FGF-140 retains the same regions of homology to acidic and basic FGF as the full-length K-FGF protein (as shown in Table 1 below) but has increased biological activity.

TABLE 1

```
 67' AAQPKE AAVQSGAGDYLLG-IKRLRRLYCNVGIGFHLQALPDGRIGGAHADTRDSL-LEL
            ..:.:..  :  .:  .:::::. : :: :.  ::::...:.....  . :.:
  1"       PA LPEDGGSGAFPPGHFKDPKRLYCKNG-GFFLRIHPDGRVDGVREKSDPHIKLQL

119' SPVERGVVSIFGVASRFFVAMSSKGKLYGSPFFTDECTFKEILLPNNYNAYESYKYPGMF
     . :::::::: ::  ..  ...::...:.: .:    :::: : : : .:::::.: : ::.. .
 56" QAEERGVVSIKGVCANRYLAMKEDGRLLASKCVTDECFFFERLESNNYNTYRSRKYSSWY

179' IALSKNGKTKKGNRVSPTMKVTHFLPRL
     .::...:.. : :  ...:. :.. :::
116" VALKRTGQYKLGPKTGPGQKAILFLPMSAKS

67' AAQPKEAAVQSGAGDYLLGIKRLRRLYCNVGIGFHLQALPDGRIGGAHADTRDSL-LELS
          :  .:.. . :::. : :. :. ::::  ...:....   .  .  .  :.:.
  1"                FNLPLGNYKKPKLLYCSNG-GYFLRILPDGTVDGTKDRSDQHIQLQLC

120' PVERGVVSIFGVASRFFVAMSSKGKLYGSPFFTDECTFKEILLPNNYNAYESYKYPGM--
     . . : : :  ....  :.::...: ::::.  ...:: : : :  :.::.: : :....
 48" AESIGEVYIKSTETGQFLAMDTDGLLYGSQTPNEECLFLERLEENHYNTYISKKHAEKHW

178' FIALSKNGKTKKGNRVSPTMKVTHFLPRL
     :...:.:::..: : :.   . :.. :::
108" FVGLKKNGRSKLGPRTHFGQKAILFLPLPVSSD

A = Ala;  R = Arg;  N = Asn;  D = Asp;  C = Cys;  Q = Gln;  E = Glu;
G = Gly;  H = His;  I = Ile;  L = Leu;  K = Lys;  M = Met;  F = Phe;
P = Pro;  S = Ser;  T = Thr;  W = Trp;  Y = Tyr;  V = Val.
```

In Table 1, the N-terminal amino acid (alanine) of K-FGF-140 is residue 67 of the full-length K-FGF protein. Two dots between a particular set of amino acid residues indicate exact identity between the truncated growth factor of the present invention and either one of basic (SEQ. ID. NO. 3) and acidic FGF (SEQ. ID. NO. 4), and one dot indicates that there has been a conservative substitution, e.g. substitution of the same type of amino acid such as phenyl-alanine substituted for tyrosine. In addition, the amino acid sequence of the truncated growth factor of the present invention are number 67'–206', while the FGF sequences are presented as 1"–146" and 1"–141" for basic and acidic FGF, respectively. That is to say residues 1"–146" comprise the sequence of basic FGF, while residues 1"–141" comprise acidic FGF.

As shown in Example 5 below, the truncated protein had mitogenic activity that is 4–5 times greater (i.e. increased DNA synthesis and cell proliferation activity) than the full-length K-FGF protein as shown by its ability to induce proliferation of 3T3 cells at concentrations 4–5 times lower than those of K-FGF. The truncated K-FGF protein also has a higher affinity for two of the FGF receptors than either the full-length K-FGF protein or basic fibroblast growth factor (bFGF).

The growth factor of the present invention can be obtained from the medium of cells transfected or transformed by the "wild type" or full-length K-FGF gene that have been cultivated in the presence of glycosylation inhibitors, such as tunicamycin. Alternatively, K-FGF-140 can be obtained from the medium of cells transfected or transformed by a mutated K-FGF cDNA that produces a protein incapable of being glycosylated, as the one described above, or preferably by using a suitable DNA construct to transform or transfect a eukaryotic, plant, or bacterial cell (e.g. E. coli), the latter described in Example 2 below. The wild type full-length gene can be obtained as described in co-pending U.S. patent application Ser. No. 07/806,771 (abandoned) filed Dec. 6, 1991. Alternatively the DNA sequence can be used to chemically synthesize the K-FGF-140 gene using techniques well known in the art.

The DNA encoding the growth factor of the present invention can be cloned and the protein can be expressed in any eukaryotic or prokaryotic system known in the art. Non-limiting examples of suitable eukaryotic expression systems include yeast expression vectors (described by Brake, A. et al., *Proc. Nat. Acad. Sci. USA* 81: 4642–4646, 1984), Polyoma virus based expression vectors (described in Kern, F. G. et al. *Gene* 43: 237–245, 1986) Simian virus 40 (SV40)-based expression vectors in COS-1 Simian cells (as described in Gething, M. J. et al. *Nature* 293: 620–625, 1981) and baculovirus (insect)-based expression vectors (described in U.S. Pat. No. 4,145,051, issued May 17, 1988 and U.S. Pat. No. 4,879,232, issued Nov. 7, 1989). An example of a procaryotic expression system (e.g. *E. coli*) is presented below in Example 2 and an example of a eukaryotic expression system (e.g. COS cells) is presented below in Example 3. Particularly preferred expression vectors include *E. coli*, simian COS cells and baculovirus (insect) cells.

The DNA encoding the truncated mammalian growth factor of the present invention may be modified without changing the primary sequence of the encoded polypeptide in order to increase the efficiency of its production. One such example is presented in Example 2 below where AT nucleotides were incorporated into the 5' end of the molecule for cloning into *E. coli*. In addition, an ATG encoding methionine, was also added to the 5' end of the DNA. Other modifications for cloning and expression in other systems are known in the art and are within the scope of the present invention.

The DNA sequence (SEQ. ID. NO. 5) of K-FGF-140 is as follows:

```
GCG GCC GTC CAG AGC GGC GCC GGC GAC TAC CTG CTG GGC        39
Ala Ala Val Gln Ser Gly Ala Gly Asp Tyr Leu Leu Gly
 1               5                  10

ATC AAG CGG CTG CGG CGG CTC TAC TGC AAC GTG GGC ATC        78
Ile Lys Arg Leu Arg Arg Leu Tyr Cys Asn Val Gly Ile
        15                  20                  25

GGC TTC CAC CTC CAG GCG CTC CCC GAC GGC CGC ATC GGC       117
Gly Phe His Leu Gln Ala Leu Pro Asp Gly Arg Ile Gly
                30                  35

GGC GCG CAC GCG GAC ACC CGC GAC AGC CTG CTG GAG CTC       156
Gly Ala His Ala Asp Thr Arg Asp Ser Leu Leu Glu Leu
 40                  45                  50

TCG CCC GTG GAG CGG GGC GTG GTG AGC ATC TTC GGC GTG       195
Ser Pro Val Glu Arg Gly Val Val Ser Ile Phe Gly Val
        55                  60                  65

GCC AGC CGG TTC TTC GTG GCC ATG AGC AGC AAG GGC AAG       234
Ala Ser Arg Phe Phe Val Ala Met Ser Ser Lys Gly Lys
                70                  75

CTC TAT GGC TCG CCC TTC TTC ACC GAT GAG TGC ACG TTC       273
Leu Tyr Gly Ser Pro Phe Phe Thr Asp Glu Cys Thr Phe
        80                  85                  90

AAG GAG ATT CTC CTT CCC AAC AAC TAC AAC GCC TAC GAG       312
Lys Glu Ile Leu Leu Pro Asn Asn Tyr Asn Ala Tyr Glu
                95                 100

TCC TAC AAG TAC CCC GGC ATG TTC ATC GCC CTG AGC AAG       351
Ser Tyr Lys Tyr Pro Gly Met Fhe Ile Ala Leu Ser Lys
105                 110                 115

AAT GGG AAG ACC AAG AAG GGG AAC CGA GTG TCG CCC ACC       390
Asn Gly Lys Thr Lys Lys Gly Asn Arg Val Ser Pro Thr
            120                 125                 130

ATG AAG GTC ACC CAC TTC CTC CCC AGG CTG TGA               423
Met Lys Val Thr His Phe Leu Pro Arg Leu
                135                 140
```

The polypeptide of the present invention can be purified by any one of the many techniques that are well known in the art for use in conjunction with the expression system to produce the polypeptide. For example, when expressing the protein in *E. coli*, a purification procedure such as that disclosed in Example 2 below may be used.

The truncated K-FGF mammalian growth factor of the present invention can be employed as a wound-healing agent for various mammalian wounds, such as decubitus ulcers or burns. When employed as a wound or burn healing agent, the growth factor of the present invention may be administered to a mammal in need of such treatment orally, parenterally, or preferably, topically, directly to the affected area in amounts broadly ranging between about 10 nanograms and about 10 micrograms per dose. The number of treatments required to treat a particular wound or burn and the duration of treatment can vary from individual to individual depending upon the severity of the wound or burn. A typical treatment would comprise 1 or 2 topical applications per day, that are applied directly to the surface of the wound or burn.

The growth factor of the present invention can be prepared in pharmaceutical formulations or dosage forms to be used as a wound or burn healing agent. Pharmaceutical formulations containing the mammalian growth factor of the present invention (or physiologically acceptable salts thereof) as at least one of the active ingredients may also contain pharmaceutically-acceptable carriers, diluents, fillers, salts and other materials well-known in the art depending upon the dosage form utilized. For example, parenteral dosage forms may comprise a physiologic, sterile saline solution. Topical dosage forms may comprise for example, lanolin, hydroxymethyl cellulose or propylene glycol. In an alternative embodiment, the mammalian growth factor of the present invention may be mixed with antibiotic creams (such as Silvadene, Marion Laboratories, Kansas City, Mich., Achromycin, Lederle Laboratories, Pearl River, N.Y., or Terramycin, Pfipharmecs, New York, N.Y.) well-known in the art.

As will be understood by those of ordinary skill in the art, the pharmaceutical formulations or dosage forms of the present invention need not contain an effective amount of the truncated protein of the present invention as such effective amounts can be achieved by administering a plurality of formulations or dosage forms.

Although the truncated K-FGF growth factor of the present invention is particularly useful as a wound or burn healing agent it also can be employed as an agent to promote the growth of cells in tissue culture and/or as a partial serum substitute. The growth-promoting properties of truncated K-FGF are illustrated in Example 5 below.

The invention is described further below in specific working examples which are intended to illustrate the present invention without limiting its scope.

EXAMPLE 1

AMINO ACID SEQUENCE OF THE HUMAN K-FGF PRECURSOR PROTEIN

The amino acid sequence of K-FGF (SEQ ID NO:12 (full-length precursor) and SEQ ID NO: 13 (full-length mature protein lacking 30–31 N-terminal amino acids)) and K-FGF-140 (SEQ ID NO:1) are shown in FIG. 1. In FIG. 1, arrows under the sequence indicate the sites of cleavage of the mature, secreted form of K-FGF. Asterisks indicate the glycosylation signal. The result of the mutation introduced in the cDNA to eliminate glycosylation is indicated above the asterisks (Threonine to Alanine). The [ sign indicates the site of cleavage which generates K-FGF-140.

EXAMPLE 2

CONSTRUCTION AND EXPRESSION VECTOR FOR K-FGF-140

The K-FGF-140 cDNA (which was mutated at the glycosylation site) was expressed in COS cells using media conditions that allowed tritiated leucine to be incorporated into the expressed protein. The leucine-labeled protein was purified by precipitation with a polyclonal antibody raised against full-length K-FGF. The amino terminus of the purified K-FGF-140 protein was sequenced using a protein sequencer (Applied Biosystems model 470A). Tritium was found in several cycles and these cycles were assigned as leucine residues. There was a major sequence and a minor sequence. By a process of elimination the major sequence was identified as starting at residue 67 of the K-FGF full-length sequence (Delli-Bovi et al. *Cell* 50: 729–37 1987, Delli-Bovi et al. 1988 *Molecular and Cellular Biology* 8: 2933–41). The sequence of this truncated protein is illustrated in FIG. 1.

A variety of different expression vectors may be used to produce the K-FGF-140 protein in *E. coli*. A bacterial expression vector was designed and constructed encoding the K-FGF-140 protein under the control of the bacteriophage lambda pL promoter and the cII ribosome binding site. The full-length cDNA sequence of K-FGF (SEQ ID NO:9) was altered using site directed mutagenesis (T. A. Kunkel et al. (1987) *Methods in Enzymol.*, Vol. 154, pages 367–382) to delete the sequence for the first 66 amino acids and place an initiator methionine in front of residue 67. It was also found desirable to change the codon usage pattern (using site directed mutagenesis) at the start of the truncated sequence to codons containing more Adenine or Thymidine. The sequence changes that were made are illustrated in Table 2 below.

shifted to 40° C. where the lambda repressor fails to repress the pL lambda promoter and maintained at this temperature for 3 hours. Cells were harvested by centrifugation and stored at −80° C. The bacterial cells were broken in the presence of break buffer (6.0 g Tris adjusted to pH 7.0 with HCl, 1.9 g EDTA, 1.7 g PMSF, 1.0 g pABA all in 1 L water) in a homogenizer (Gaulin model 15). The cells were passed three times through the homogenizer at a pressure differential of 8000–9000 pounds per square inch (PSI). The broken cell paste was frozen in liquid nitrogen and stored at 80° C.

Most of the K-FGF-140 protein,was found in the insoluble fraction in the cell lysate and was harvested by centrifugation. The growth factor was extracted from the centrifugation pellet by suspension in extraction buffer (50 mM Tris pH 7.5, 200 mM $MgCl_2$). The extract was centrifuged and K-FGF-140 was found in the soluble fraction. This fraction was loaded onto a heparin Toyopearl (Tosohaas) column, and the buffer exchanged with 0.5M NaCl, 50 mM Tris pH 7.5 followed by 0.5M NaCl, 20 mM Na phosphate pH 7.5. Finally, the K-FGF-140 protein was eluted with a gradient of 0.5–1.75 NaCl in 20 mM Na phosphate pH 7.5. The protein was found to elute at a salt concentration of about 1.55 M NaCl whereas full-length K-FGF elutes at about 1.15 M NaCl.

EXAMPLE 3

IMMUNOPRECIPITATION ANALYSIS OF THE K-FGF FORMS PRODUCED IN COS CELLS TRANSFECTED WITH THE GLYC-K-FGF-140 cDNA

COS cells were transfected with the 91203B expression plasmid (described in Delli-Bovi et al. (1987) *Cell*, Vol. 50, pages 729–737) containing either the full-length human K-FGF cDNA or a mutated cDNA encoding a protein lacking the N-linked glycosylation signal (glyc(−)cDNA). 40. hours later the cells were labelled with $^{35}$S-methionine for 8 hours, in the presence (+) or absence (−) of tunicamycin, a drug that inhibits N-linked glycosylation. Labelled proteins from either the cell lysate (indicated as L) or medium (indicated as M) were immunoprecipitated with anti-K-FGF rabbit antibodies and electrophoresed on SDS-PAGE. The gel was then subjected to autoradiography. The results are shown in FIG. 2.

In FIG. 2, M.W. markers are indicated on the right. It can be seen that the cell transfected with the glyc(−)cDNA

TABLE 2

| | | |
|---|---|---|
| Original Sequence | (SEQ ID NO:6) | GCG GCC GTC CAG AGC GGC GCC GGC GAC |
| New Sequence | (SEQ ID NO:7) | ATG GC<u>A</u> GC<u>A</u> GT<u>T</u> C<u>AATCA</u> GG<u>A</u> GC<u>A</u> GGC |
| Amino Acid | (SEQ ID NO:8) | Met Ala Ala Val Gln Ser Gly Ala Gly Asp |

In Table 2, the nucleotides which were changed are underlined. None of the changes resulted in a change in the amino acids sequence of the protein.

Other changes to more favorable codons or changes further into the sequence could also have been made. This AT rich sequence at the start of the gene was found to optimize the amount of K-FGF-140 protein expressed in *E. coli* B4.

The K-FGF-140 gene was expressed in *E. coli*.

Expression of the gene was accomplished by growing cells at 30° C. (the permissive temperature for the temperature sensitive lambda repressor). The culture was then expressed in the cell lysate a protein of apparent M.W. of 18,000 Daltons, identical to the one produced by the wild-type K-FGF DNA in the presence of tunicamycin. This protein cannot however, be detected in the culture medium, where only two bands of MW 12,000–14,000 were seen.

EXAMPLE 4

ELUTION OF K-FGF-140 FROM HEPARIN AFFINITY COLUMNS

Figure 3:
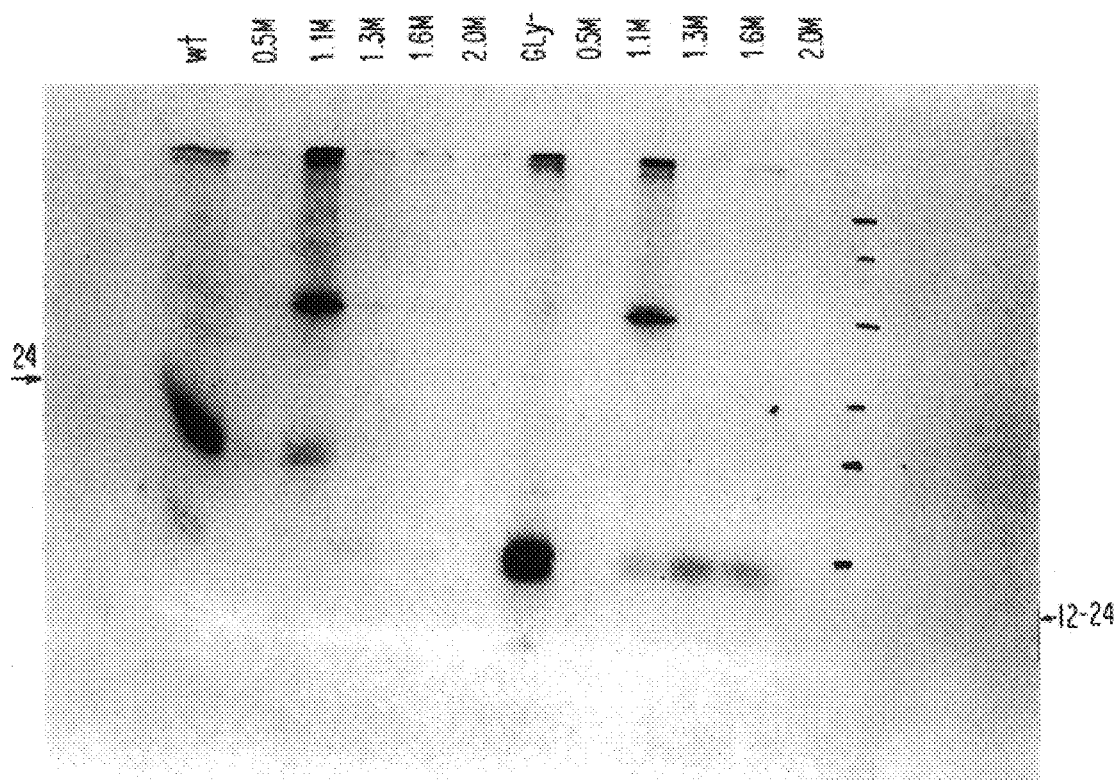
FIG. 3 is an autoradiograph of an SDS-PAGE analysis of the elution of K-FGF and K-FGF-140 from heparin affinity columns.

Conditioned Medium labeled with $^{35}$S-methionine produced from COS cells transfected with either of K-FGF or glyc-cDNAs (i.e. K-FGF-140) was absorbed to Heparin- Sepharose columns and eluted with increasing salt concentrations. Fractions were immunoprecipitated with anti-K-FGF antibodies, and electrophoresed on SDS-PAGE to identify the K-FGF proteins. The results are shown in FIG. 3.

It can be seen that all or most of K-FGF eluted at 1.1 M NaCl, while the truncated K-FGF forms eluted with a peak at 1.3–1.6 M NaCl.

EXAMPLE 5

STIMULATION OF DNA SYNTHESIS IN QUIESCENT BALB/c-3T3 CELLS BY HUMAN RECOMBINANT K-FGF OR BY RECOMBINANT K-FGF-140

BALB/c-3T3 cells were incubated for two days in medium containing 0.5% serum, at which point cells were treated with different concentrations of K-FGF or K-FGF-140. 18 hours later the cells were labeled with $^3$H-thymidine (1 $\mu$Ci/ml) for 6 hours. Radioactivity incorporated into cellular DNA was counted after trichloroacetic acid (TCA) precipitation. The results are shown in FIG. 4.

Figure 4:
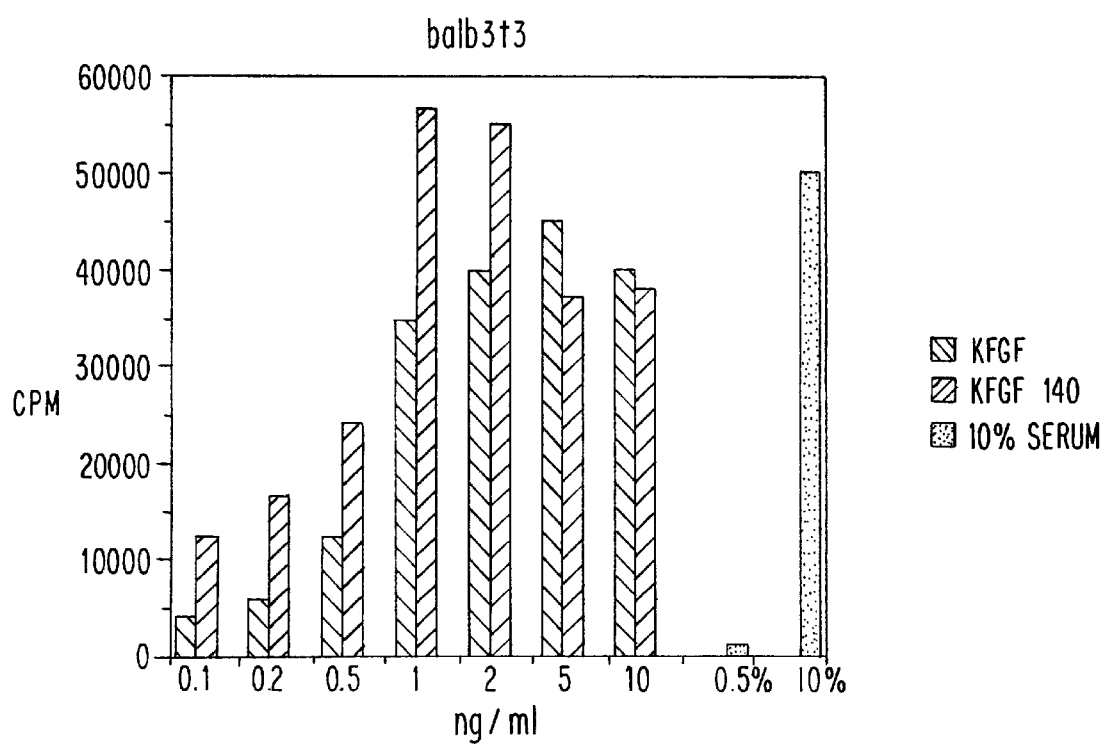
FIG. 4 is a graph showing the stimulation of DNA synthesis in quiescent BALB/c-3T3 cells by recombinant K-FGF and K-FGF-140.
Figure 5A:
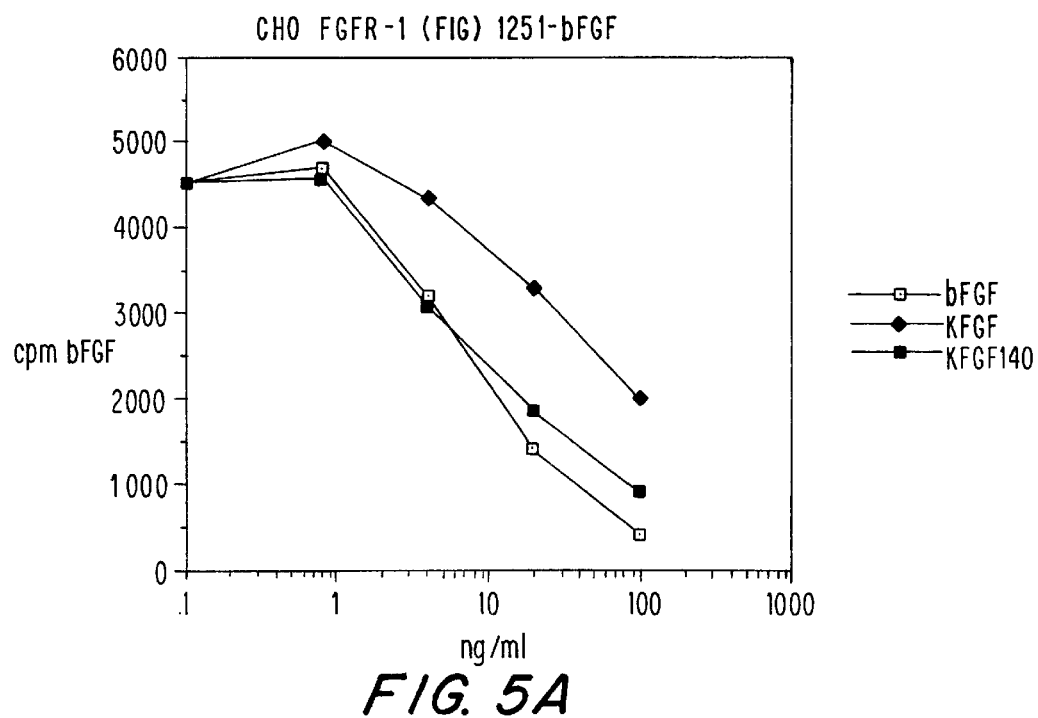
FIGS. 5 (A and B) are graphs depicting a competition assay of the ability of K-FGF and K-FGF-140 to displace labeled basic fibroblast growth factor (bFGF) binding to Chinese Hamster Ovary (CHO) cells expressing the FGF receptor 1 (flg) or 2 (bek).
Figure 5B:
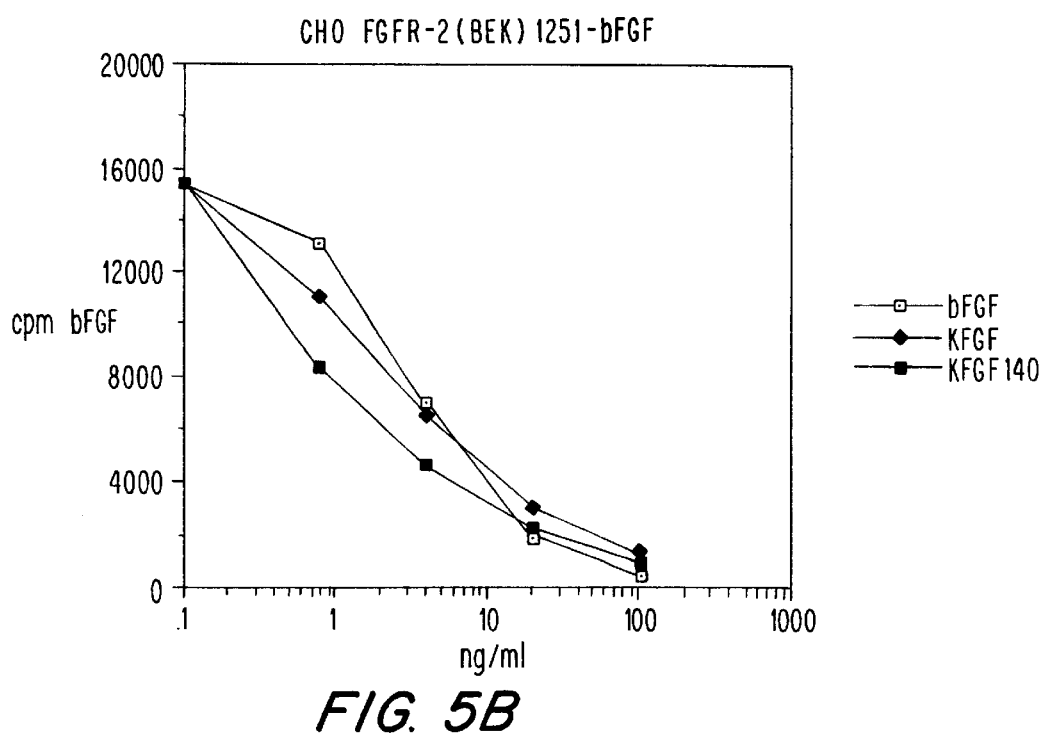

In FIG. 4, 0.5%=negative control, 10%=cells stimulated with 10% serum. As can be seen from the data in FIG. 5, 0.1 ng of K-FGF-140 was capable of producing the same stimulation of DNA synthesis as that of 0.5 ng of K-FGF. Furthermore, maximum stimulation in $^3$H-thymidine uptake occurred using 1 ng/ml of K-FGF-140 and 5 ng/ml full-length K-FGF. Treatment with 1 ng/ml of K-FGF-140 led to a greater amount of cell proliferation than all other additions, including 10% serum.

EXAMPLE 6

RECEPTOR BINDING

To study the affinity of K-FGF-140 for FGF receptors, the ability of K-FGF and K-FGF-140 to compete with $^{125}$I-labeled basic fibroblast growth factor (bFGF) for binding to CHO 4-1 cells expressing FGF receptor-1 (Mansukhani, A. et al. (1992) *Proc. Natl. Acad. Sci. USA*, Vol. 89, pages 3305–3309) (A) or to CHO 3–7.5 cells expressing the FGF receptor-2 (Mansukhani, A. et al. (1990) *Proc. Natl. Acad. Sci. USA*, Vol. 87, pages 4378–4382) (B) was performed. Cells (1×10$^6$ cells/35 mm dish) were incubated at 4° C. with Dulbecco's modified EAGLE's medium (DMEM) containing 0.15% gelatin, 25 mM Hepes (pH 7.4), Heparin (10 $\mu$g/ml), $^{125}$I-labeled bFGF (4 ng/ml s.a. 3.2×10$^{17}$ cpm/mole, Collaborative Research) and the indicated concentration of unlabeled bFGF, K-FGF or K-FGF-140. After 2 hours the cells were washed with 2M NaCl buffered at pH 7.4 to remove growth factor bound to the matrix, and with 2M NaCl buffered at pH 4.0 to remove the ligand bound to high affinity receptors. The amount of $^{125}$I-labeled bFGF bound to high affinity receptors was determined. The results are shown in FIGS. 5 (A and B).

In the CHO clone expressing the FGF receptor 1 (FIG. 5A) the data show that about 8 times more K-FGF than bFGF or K-FGF-140 was needed to compete for the binding of $^{125}$I-labeled bFGF; in the CHO clone expressing the FGF receptor 2 (FIG. 5B), K-FGF-140 was more efficient than K-FGF and bFGF in competing for the binding of $^{125}$I-labeled bFGF. In this case the affinity of K-FGF-140 for the receptors was about three times higher than that of bFGF or full-length K-FGF.

EXAMPLE 7

COMPETITION BETWEEN K-FGF AND K-FGF-140 FOR RECEPTOR BINDING

Figure 6A:
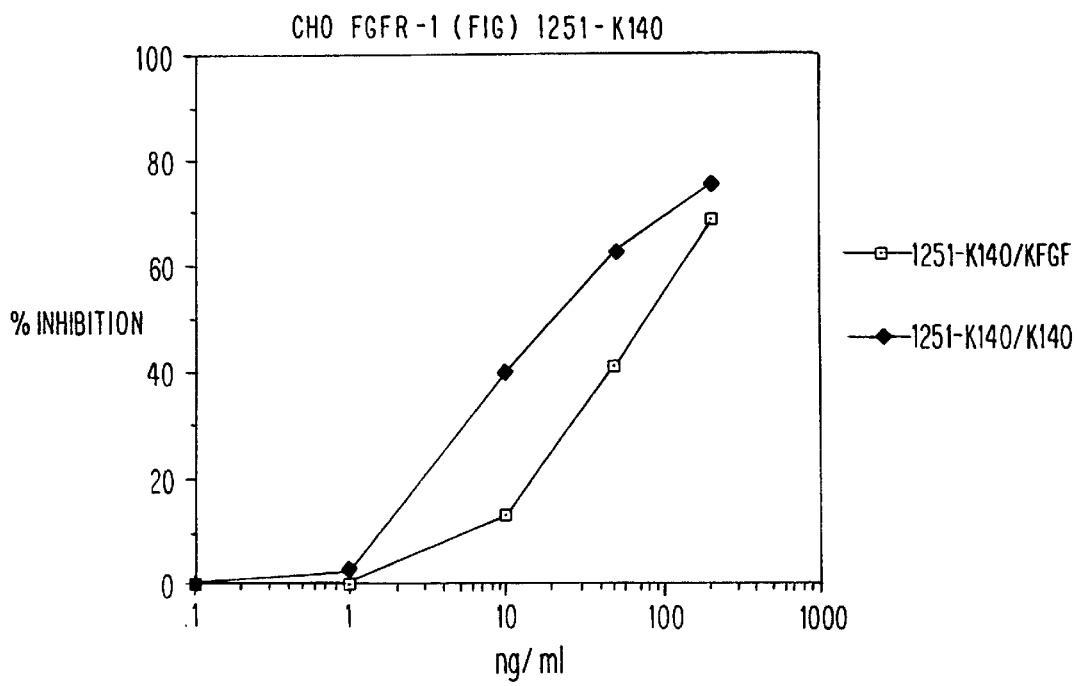
FIGS. 6 (A–D) are a series of graphs depicting competition assays between K-FGF and K-FGF-140 for receptors on CHO cells expressing the FGF receptor 1 (flg) or 2 (bek).
Figure 6B:
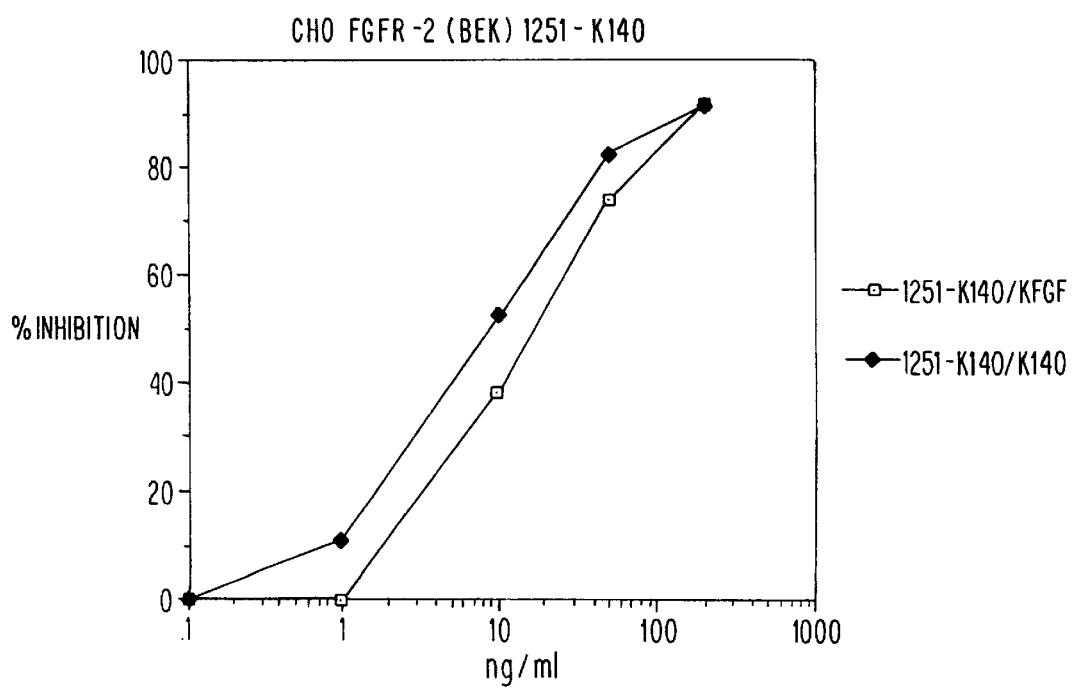
Figure 6C:
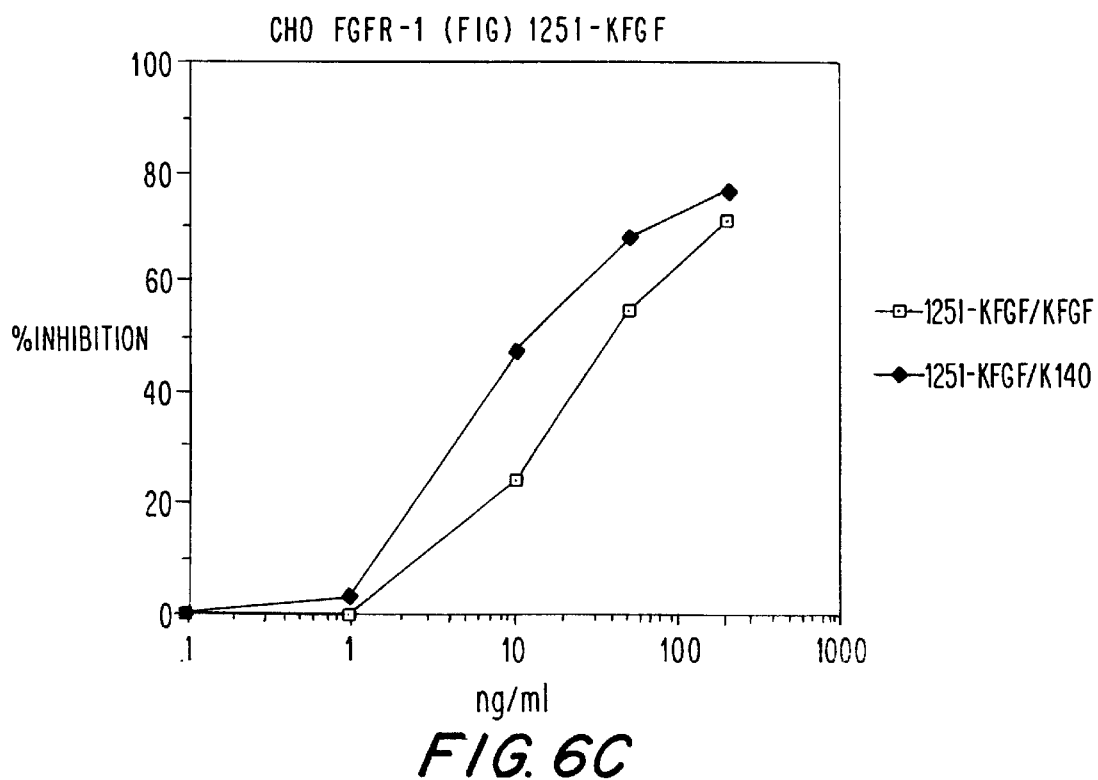
Figure 6D:
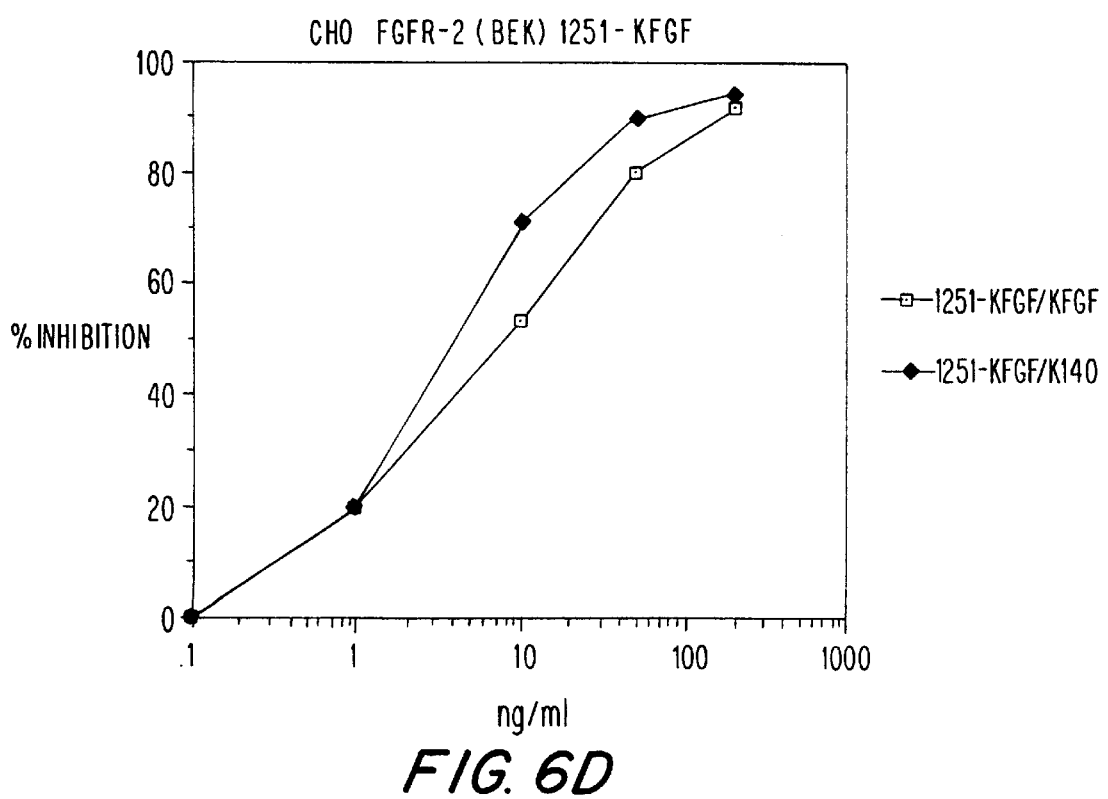

Clones CHO 4-1 expressing FGF receptor-1 (FIG. 6A and FIG. 6C) or CHO 3–7.5 expressing FGF receptor-2 (FIG. 6B and FIG. 6D) were incubated with $^{125}$I-labeled K-FGF-140 (11 ng/ml, specific activity 7.7×10$^{16}$ cpm/mole) (FIGS. 6A and B) or with $^{125}$I-labeled K-FGF (8 ng/ml, specific activity 9.9×10$^{16}$ cpm/mole) (FIGS. 6C and D), Heparin (10 ug/ml) and the indicated concentration of unlabeled K-FGF or K-FGF-140. After 2 hours at 4° C. the medium was removed, the cells were washed with ice cold Tris and were lysed in 0.6% SDS/50 mM. Tris/HCl pH 7.4, 0.15M NaCl, 5 mM. EDTA, and the cell associated radioactivity was determined. The data are expressed as % of inhibition of Iodine labeled growth-factor binding by the indicated amount of unlabeled growth factor.

The data presented in FIG. 6 show that K-FGF-140 had a higher affinity for both FGF (FIGS. 6A and 6C and FIGS. 6B and 6D) receptors than full-length K-FGF protein.

EXAMPLE 8

SCATCHARD ANALYSIS OF K-FGF AND K-FGF-140 BINDING TO CHO CELLS EXPRESSING THE FLG RECEPTOR

Scatchard analysis of the binding of K-FGF and K-FGF-140 was performed on CHO 4-1 cells expressing the FGF receptor-1 as follows. Cells at 4.8×10$^5$/35mm dish were incubated at 4° C. with DMEM containing 0.15% gelatin, 25 mM. Hepes(pH 7.4), Heparin (10 ug/ml) and various concentration of $^{125}$1-labeled K-FGF or K-FGF-140 from 0.15 to 20 ng/ml. After 2 hours the medium was removed, the cells were washed with ice cold Tris and $^{125}$I-labeled K-FGF or K-FGF-140 bound to high affinity receptors was removed by extraction in 0.6% SDS/50 mMTris/HCl pH 7.4, 0.15 mM NaCl, 5 mM EDTA. Non-specific binding was obtained using the same amount of growth factor on parental CHO DG44 cells that do not express FGF receptors. The results are shown in FIG. 7.

Figure 7:
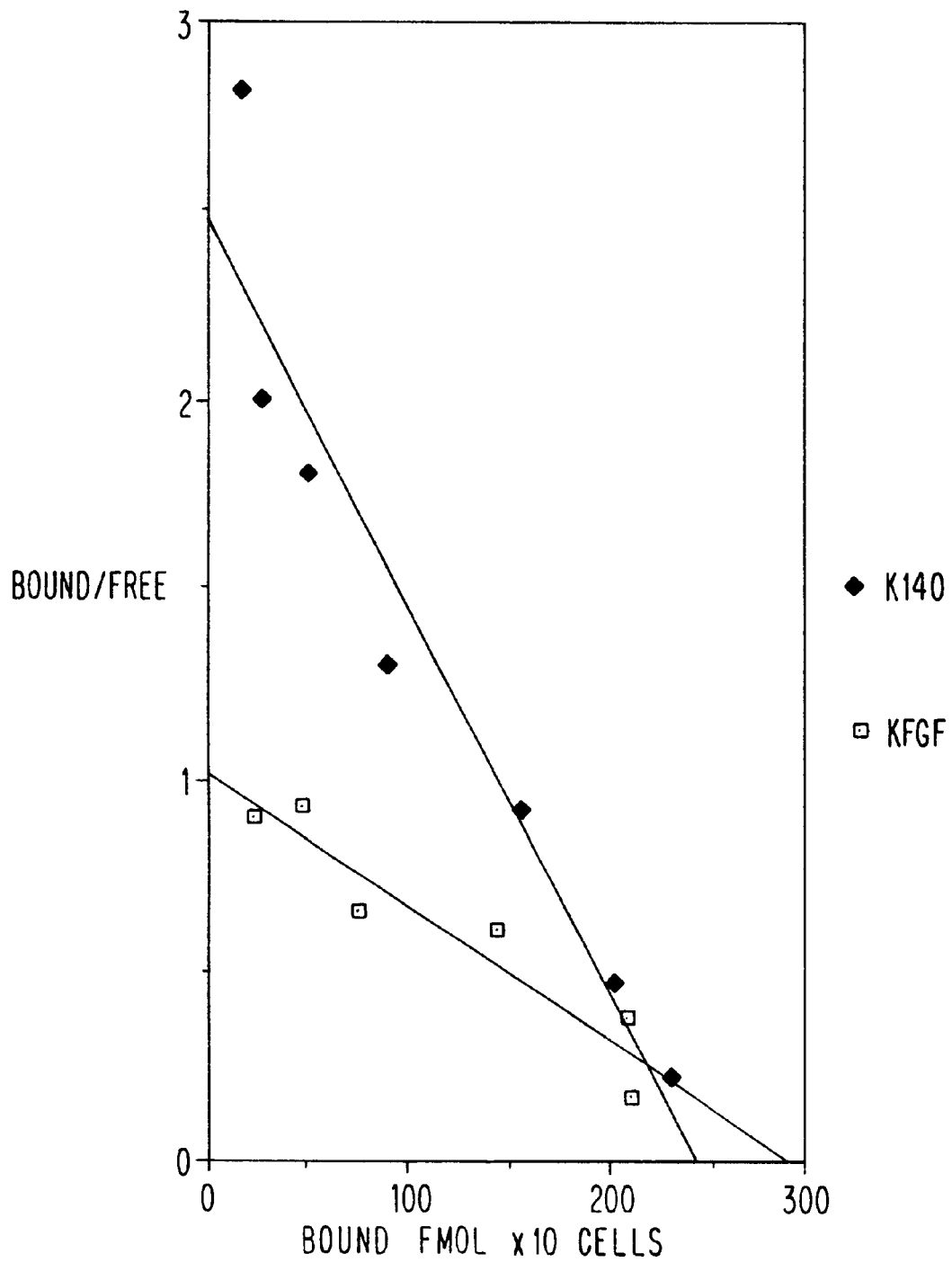
FIG. 7 is a graph depicting a Scatchard analysis of K-FGF and K-FGF-140 binding to CHO cells expressing the FGF receptor 1 (bek).

In FIG. 7, Scatchard analysis of binding to high affinity receptors gave a straight line, indicating a single class of binding sites. The data also indicate that the average binding affinity of K-FGF-140 for the flg receptor is about 9.5×10$^{-11}$ M or about three times higher than that of full-length K-FGF which has an average binding affinity of about 28.5×10$^{-11}$M.

EXAMPLE 9

WOUND HEALING ASSAY

K-FGF-140 will be assayed in an ischemic wound healing system. For this purpose the rabbit ear ischemic model of dermal ulcers, in which healing of these ulcers is retarded because of induced ischemia (reduced blood flow) is used. After wounding (6 mm wounds) K-FGF-140 is applied either in an isotonic buffer or in a gel, applied in a single dose (1–5 $\mu$g), and compared to untreated controls, or wounds treated with K-FGF or bFGF. At various days after the beginning of the experiment (up to day 7–10) the extent of wound healing is determined by measuring a) new epithelium formed at the gap of epithelia tissue at the beginning and end of the experiment) by histological cross sections; b) the gap between the two edges of the granulation tissues; and c) formation of new granulation tissue as measured by staining of immature vs. mature collagen. These techniques are described in Ahn, S. T. and Mustoe, T. A. *Annals Plastic Surgery* 24: 17–23 (1990) and Mustoe, T. A., Pierce G. F., Morishima, C. and Deuel, T. P. *J. Clinical Invest.* 87: 694–703 (1991).

From the in vitro experiments present above showing that K-FGF-140 has higher potency and receptor affinity then K-FGF, it is expected that K-FGF-140 will prove effective at accelerating wound healing in the system, and will prove more potent (effective at lower concentration, faster response) than K-FGF or bKFGF.

EXAMPLE 10

TRANSFECTION OF NIH3T3 CELLS

High molecular weight DNA was extracted from one KS skin lesion, as described in Delli Bovi, P. et al, *Cancer Res.* 46: 6333–6338, 1986, (incorporated by reference) and transfected into NIH3T3 cells using the well-known calcium phosphate precipitation technique (Graham, F. L. et al *Virology* 52: 456–467, 1973). A distinct focus of highly refractile cells was produced over the background of non-transfected NIH3T3 cells indicating the presence of transformed cells. To insure the homogeneity of the cell population, cells from the primary focus were recloned in agar suspension medium (Stoker, M. et al *Nature* 203: 1355–1357, 1964 incorporated by reference) since only transformed cells are capable of such growth.

Southern blot hybridization, performed with the Blur-8 plasmid (Jelinek, W. R. et al *Proc. Nat. Acad. Sci. USA* 77: 1398–1402, 1980 incorporated by reference), containing DNA sequences representative of the AluI family of repetitive DNA (a repetitive DNA sequence present in and indicative of DNA isolated from human cells), revealed that transformed all cells capable of growth in agar had acquired human DNA sequences.

Cells from one agar colony isolated as above, were injected into athymic mice ($10^8$ cells per mouse) and two out of three mice developed tumors. DNA from one of the tumors (A15T) was used to transfect NIH3T3 cells together with a selectable marker, plasmid plW3 (Pellegrini, S. et al *Cell.* 36: 943–949, 1984 incorporated by reference) which contains sequences conferring resistance to the aminoglycoside antibiotic neomycin or G418 (a neomycin derivative). Mammalian cells, such as NIH3T3 cells, are sensitive to and are killed by these aminoglycoside antibibtics. However, plasmid plW3 encodes a gene which allows cells to grow in the presence of neomycin or G418. Selection for cells resistant to G418 revealed the presence of two colonies with transformed morphology, such as a disorganized piling of cell, and a loss of contact inhibition of growth, while selection for focus formation also resulted in the isolation of two morphologically transformed foci.

DNA from one of the colonies resistant to neomycin was used for a third cycle of NIH3T3 transfection and again produced a small but significant number of AluI positive transformed foci. This demonstrated that the human DNA sequences identified and used to transfect NIH3T3 cells were capable of reproducibly transforming these cells, since the transformed phenotype correlated with the presence of the human AluI repetitive DNA in every stage of the assay.

EXAMPLE 11

MOLECULAR CLONING

A genomic library of DNA extracted from one of the neomycin-resistant secondary transformants (Neo-2) was constructed after endonuclease MboI partial digestion and cloned into the EMBL3 lambda phage vector (Frischauf, A. M. et al *J. Mol. Biol.* 170: 827–842, 1983 incorporated by reference). The library was screened for the presence of recombinant phages containing human AluI repetitive DNA by plating the recombinant phages on a lawn of phage-susceptible bacteria, and allowing them to form plaques of bacterial lysis. Phage DNA was collected from the individual lysates and transferred to nitrocellulose filters (Schleicher and Schul, Keene, N.H.) and hybridized with a nick-translated, $^{32}$P-labeled purified 300 basepair BamHI restriction fragment from plasmid Blur-8 (as described in Maniatis et al, *Molecular Cloning: A Laboratory Manual.* Cold Spring Harbor Lab, N.Y., 1982). One recombinant phage (KS-2) was isolated by this procedure. Hybridization with the Blur-8 AluI plasmid and total mouse DNA revealed that it contained one AluI sequence and two stretches of repetitive mouse DNA sequences and, thus represented one of the junctions between mouse and human DNA in the secondary Neo-2 transformant.

Figure 8:
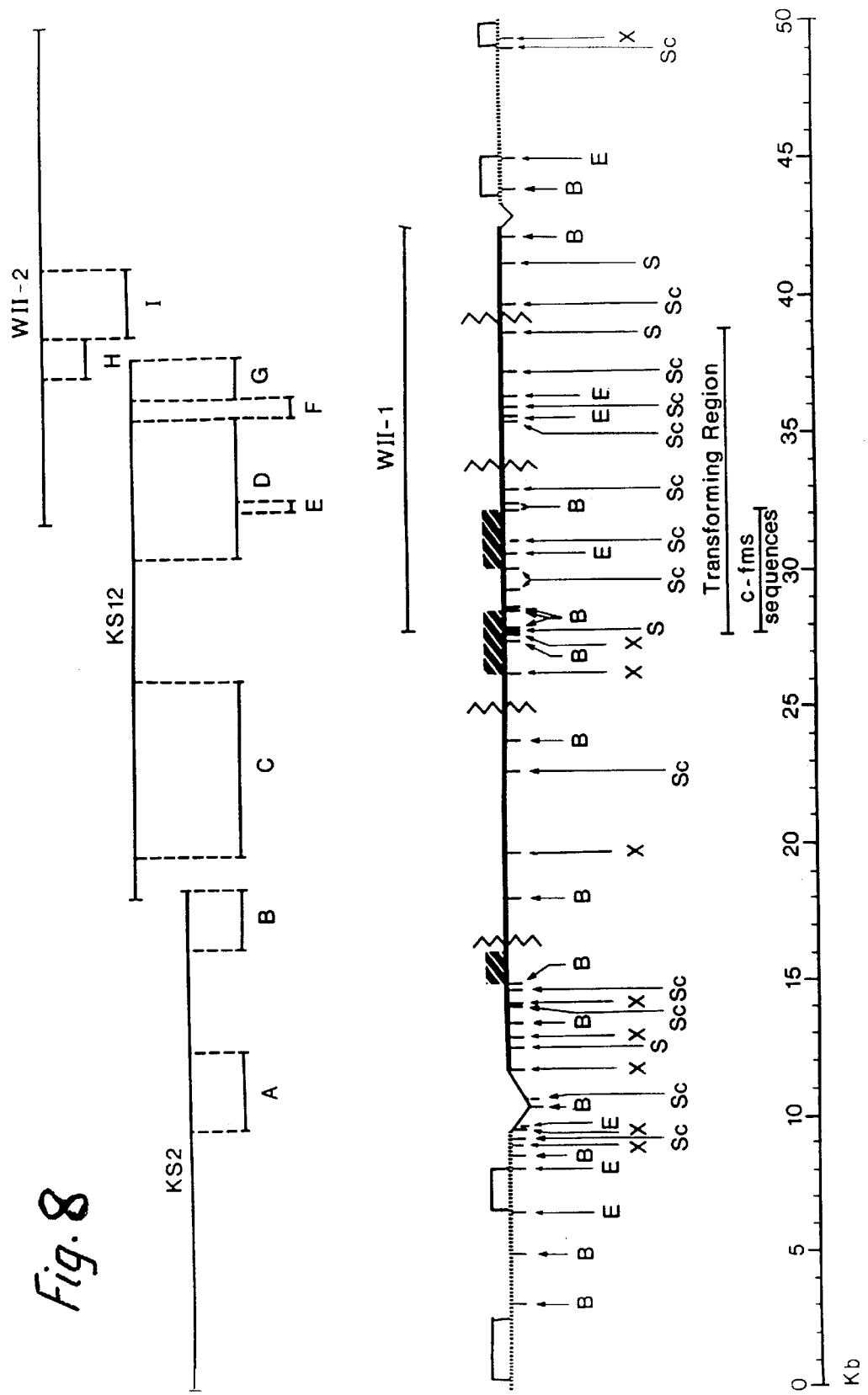
FIG. 8 is a schematic representation of the organization of the human DNA sequences (and probes made thereto) inserted into the mouse genome in the secondary Neo-2 transformant.

Several restriction enzyme fragments indicated in FIG. 8 were used to perform two further rounds of screening of the same library by hybridization to the above-mentioned DNA fragments. Several recombinant phages were thus isolated which appeared to span the entire insertion of human DNA into the Neo-2 transformant. The restriction map of the human genomic DNA sequences present in the transfected cells as reconstructed from four overlapping recombinant phages among those isolated is shown in FIG. 8.

In FIG. 8, A, B, C, D, E, F, G, H, and I in the upper part of the figure represent DNA fragments derived from the phages shown and used in the characterization of these sequences by Southern and Northern blotting analysis. The interrupted lines indicate mouse DNA. The continuous dark lines indicate human DNA. The "V" indicates the regions of joining between mouse and human DNA. Open boxes indicate regions containing mouse repetitive DNA. The hatched boxes indicate the regions containing the human AluI repetitive DNA sequences. Squiggles indicate the approximate sites of DNA rearrangements. Restriction sites are indicated as follows: E, EcoR1; B, BamHI; X, XbaI; S, SalI, Sc, SacI.

The restriction map presented in FIG. 8 encompasses approximately 32 Kb (from the X at approximately 12 kb to just before the V at the 43 Kb marker in FIG. 1) of human DNA and contains 3 AluI sequences. Several DNA fragments derived from these sequences in FIG. 8 were used to determine the presence and arrangement of the transfected human DNA in primary and secondary transformants, as well as in normal human DNA. Southern blot hybridization using these probes revealed that all these sequences studied were present in the secondary and tertiary transformants, in the two primary tumors, and also in the DNA isolated from the primary focus (primary transformant). Restriction enzyme analysis and blot hybridization of the cloned human sequences revealed that they contained four rearrangements with respect to normal human DNA, i.e. they were derived from the junction of five DNA fragments which are normally not contiguous in the human genome.

EXAMPLE 12

TRANSCRIPTION OF HUMAN SEQUENCES PRESENT IN NIH3T3 TRANSFORMANTS

In order to detect whether the specific human sequences present in the secondary NIH3T3 transformants were transcribed into mRNAs (and presumably translated into protein) in the transfected NIH3T3 cells, several of the DNA fragments indicated in FIG. 8 (A through H) were used as probes in Northern blot hybridization. Total RNA from the secondary transformants was extracted and purified by the guanidinium-cesium chloride method as described in Kern, F. G. et al *Mol. Cell. Biol.* 5: 797–807, 1985 incorporated by reference. Poly (A)+RNA was selected (using Hybond m-AP paper, Amersham, Arlington Heights, Ill.), and RNAs were fractionated in the presence of formaldehyde by agarose gel electrophoresis and transferred to nitrocellulose filters as described by Maniatis et al. (supra). Nucleic acid hybridization, washing and autoradiography were performed as described in Kern et al (supra). The results are shown in FIG. 10.

Figure 10:
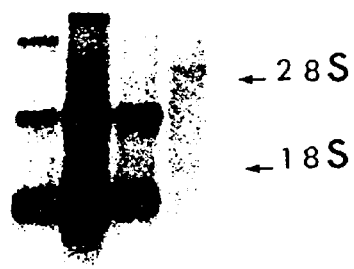
FIG. 10 is an autoradiograph of a Northern blot showing the novel mRNA species encoding the polypeptide of the present invention.
Figure 10:
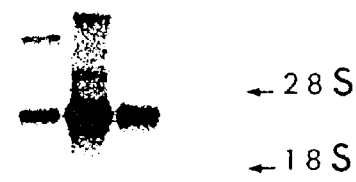

FIG. 10 shows the results of the Northern blot using probes G and H to detect novel m-RNA species in transformants by hybridization to 1.5 micrograms of poly(A)+RNA prepared from NIH3T3(lane 1); secondary transformant (designated F1A1) (lane 2); secondary transformant (Neo-2) (lane 3); A15T tumor cells (lane 4); human umbilical vein endothelial cells transformed by SV40 (designated HUVE-SV, lane 5).

Figure 9:
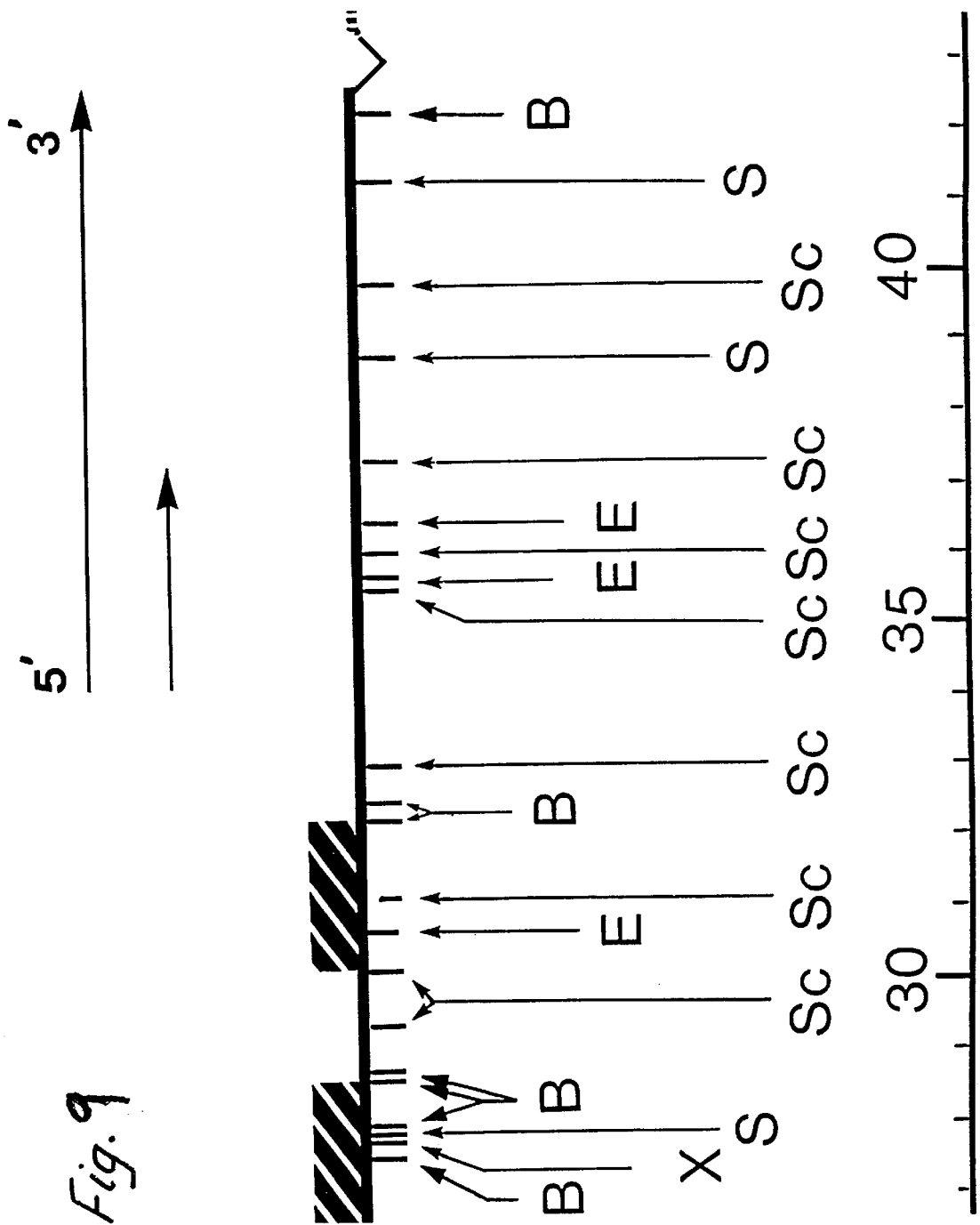
FIG. 9 is a schematic representation of the specific region of human DNA sequences shown in FIG. 8 encoding the polypeptide of the present invention.
Figure 11:
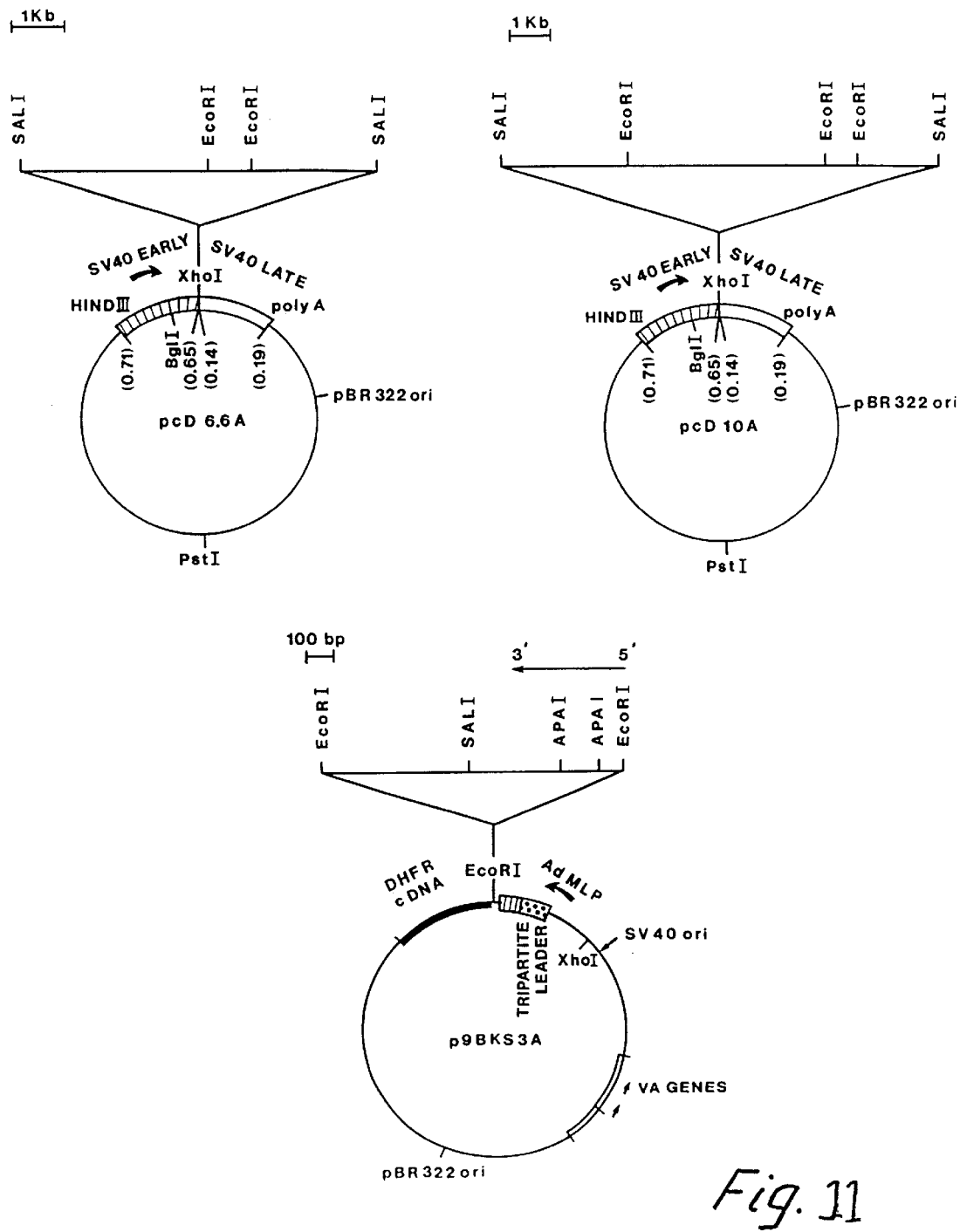
FIG. 11 is a schematic representation of the plasmids used in cloning the genomic DNA fragments and the cDNA encoding the polypeptide of the present invention.

Probes A, B, C, D, and E (identified in FIG. 8) did not hybridize with any distinct mRNA species among the poly (A)+RNAs extracted from primary or secondary transformants. Probes F and G (FIG. 10) hybridized with two novel mRNA species of about 1.2 and 3.5 Kb (FIG. 10, Panel A) in primary and secondary transformants and also with some larger RNA species of variable length in some of the cell lines tested (e.g., FIGS. 10A and B, lanes 2 and 3). These probes did not detect any distinct RNA species in normal, non-transfected NIH3T3 cells (FIGS. 10A and B, lane 1) and only a faint band of approximately 4 Kb in length in the RNA extracted from human endothelial cells (lane 5, Probe G in FIG. 11 A). Probe H recognized only the longer mRNA, but not the 1.2 Kb species (Panel B). Thus, it appeared that the transcribed sequences were restricted to about 10 Kb of human DNA, and they were expressed in these two novel species of mRNA which contain common and unique sequences. An enlargement of the map of FIG. 8 showing the region encoding these sequences is shown in FIG. 9 (indicated by the arrow 5'-3').

EXAMPLE 13

BIOLOGICAL ACTIVITY

To map more precisely the transforming DNA sequences, a 11 Kb fragment going from the left polylinker SalI (at about 28 Kb in FIG. 9) site of phage WII-1 rightward to the next SalI site (FIG. 9) was subcloned into the XhoI site of the pCD SV40 expression vector (Okayama, H. et al, *Mol. Cell. Biol* 3: 280–289, 1983, incorporated by reference), in both orientations with respect to the SV40 promoter, and the resulting plasmids (pCD10A and pCD10B, shown in FIG. 11) were tested for their biological activity. Both plasmids produced transformed foci on mouse NIH3T3 cells and rat F2408 cells with an efficiency comparable to that of a control plasmid (pTB-1) containing an activated ras oncogene (as described in Goldfarb, H. et al, *Nature* 296: 404–409, 1982 incorporated by reference).

Cells (approximately 1×10⁶ per dish) were transfected using the calcium phosphate precipitation technique as described above with the plasmid DNA together with 20 micrograms of mouse carrier DNA. Each culture was then subdivided into five plates. Foci were counted at 2–3 weeks after transfection. The results are presented below in Table 3.

TABLE 3

Transformation of Mouse and Rat Fibroblasts with Recombinant Plasmid DNAs

| Plasmids | Foci/microgram DNA | |
|---|---|---|
| | NIH3T3 | Rat F2408 |
| EXPT. I | | |
| pCD (WII-1) 10 A* | 900 | 192 |
| pCD (WII-1) 10 B* | 800 | — |
| pGEM (WII-1) 10 | 120 | — |
| pTB-1 (ras) | 800 | 520 |
| EXPT. II | | |
| pCD (WII-2) 6.6 A* | 2500 | 150 |
| pCD (WII-2) 6.6 B* | 1400 | 80 |
| pGEM (WII-2) 6.6 | 40 | — |
| pTB-1 | 2500 | 400 |
| EXPT. III | | |
| pTB-1 | 500 | — |
| p9BKS3A** | 2000 | — |
| p9BKS3B** | <1 | — |
| pCD (WII-1) 10 A | 1400 | — |

*A and B indicate the position of the SV40 promoter/enhancer element with respect to the polarity of transcription (going from left to the right in FIG. 1) of the inserted SalI genomic fragments contained in the pCD expression vector. The "A" constructs have the SV40 promoter/enhancer in 5' position and the "B" constructs in 3' position.
**The p9BKS3 plasmids contain the cDNA encoding the growth factor of the present invention in the 5'-3' polarity (A) or 3'-5' polarity (B).

As can be seen from Table 3 above, the same DNA fragment was capable of producing transformed foci when inserted into the pCD and pGEM3 bacterial vector (the latter available from Promega Biotech, Madison, Wis.), but in the case of the pGEM3 vector, with about 8-fold lower efficiency.

A 6.6 Kb DNA fragment going from the left SalI site of phage WII-2 to the same SalI site used for the above-mentioned constructs (FIG. 8) was also cloned using both pCD and pGEM vectors. The pCD 6.6 constructs transformed both mouse and rat cells with high efficiency similar to that of pTB-1 and that of the pCD10 plasmids, whereas the pGEM constructs were transformed with an efficiency about 40 fold lower (Experiment 11, Table 3). Therefore the 6.6 Kb fragment appeared to contain all of the sequences encoding a transforming gene and also a transcriptional promoter since it functioned in a plasmid vector devoid of any mammalian transcriptional regulatory elements. The higher efficiency of transformation of the pCD plasmids is probably due to the presence of the SV40 "enhancer" sequences.

EXAMPLE 14

C-DNA CLONING

To precisely identify the DNA sequences responsible for the growth factor activity of the cloned DNA products, a complementary DNA (cDNA) library was constructed from the poly(A)+RNA isolated from one of the transformants (A15T). This library was constructed in a bacteriophage lambda gt10 vector (Huynh, T. V. et al in *DNA Cloning: A Practical Approach* D. Glover, ed. Vol 1: 49–78, Oxford Press, 1985 incorporated by reference), and the recombinant phages plaques (from Example 2) screened with the probes G and H (in FIG. 8). The library was constructed using a cDNA synthesis system (Amersham. Corporation, Arlington Heights, Ill.) and the poly(A)+RNA obtained from the A15T cell line isolated by the guanidium-isothiocyanate procedure as described in Example 12 above. Following methylation with EcoRI methylase and the addition of EcoRI linkers, the linkers were digested and the cDNA size-fractionated by column chromatography (A50 m column, BioRad, Richmond, Calif.). The cDNA was then ligated to EcoRIdigested, dephosphorylated, lambda-gt10 arms (Promega Biotech, Madison, Wis.). The ligated cDNA was then packaged (using Gigapack extracts, Stratagene Cloning Systems, San Diego, Calif.) and plated, using C600 Hf1 (*E. coli*) as a host strain. A cDNA corresponding to the 1.2 Kb mRNA was isolated by plaque hybridization to probe G.

Subcloning of the cDNA insert cD3, a clone which contained the cDNA corresponding to the 1.2 Kb mRNA above, into mammalian expression vector 91023B (Kauffman, R. J. Proc. Nat. Acad. Sci. USA 82: 689–693, 1985 incorporated by reference) produced plasmid p9BKS3A and its biological activity was confirmed, i.e. it was capable of transforming NIH3T3 cells with a high efficiency upon transfection (Table I, Expt III). This cDNA was also subcloned into pGEM-3 sequencing vector (Promega Biotec, Madison, Wis.) and sequenced by the dideoxy method of Sanger, F. (Proc. Nat. Acad. Sci. USA 74: 5463–5467, 1977 incorporated by reference) and in part by the method of Maxam, A. U. and Gilbert, W. (Methods Enzymol 65: 499–560, 1980, incorporated by reference). The nucleotide sequence (SEQ ID NO: 11) is presented below.

```
                    10          20          30          40
                    *           *           *           *
            GG CGC GCA CTG CTC CTC AGA GTC CCA GCT CCA GCC GCG CGC TTT CCG 50          60          70          80          90
            *           *           *           *           *
            CCC GGC TCG CCG CTC CAT GCA GCC GGG GTA GAG CCC GGC GCC CGG GGG 100         110         120         130         140
                *           *           *           *           *
            CCC CGT CGC TTG CCT CCC GCA CCT CCT CGG TTG CGC ACT CCC GCC CGA 150         160         170         180         190
                    *           *           *           *           *
            GGT CGG CCG TGC GCT CCC GCG GGA CGC CAC AGG CGC AGC TCT GCC CCC 200         210         220         230
                        *           *           *           *
            CAG CTT CCC GGG CGC ACT GAC CGC CTG ACC GAC GCA CGC CCT CGG GCC 240         250         260         270         280
            *           *           *           *           *
            GGG ATG TCG GGG CCC GGG ACG GCC GCG GTA GCG CTG CTC CCG GCG GTC
                Met Ser Gly Pro Gly Thr Ala Ala Val Ala Leu Leu Pro Ala Val 290         300         310         320         330
            *           *           *           *           *
            CTG CTG GCC TTG CTG GCG CCC TGG GCG GGC CGA GGG GGC GCC GCC GCA
            Leu Leu Ala Leu Leu Ala Pro Trp Ala Gly Arg Gly Gly Ala Ala Ala 340         350         360         370         380
                *           *           *           *           *
            CCC ACT GCA CCC AAC GGC ACG CTG GAG GCC GAG CTG GAG CGC CGC TGG
            Pro Thr Ala Pro Asn Gly Thr Leu Glu Ala Glu Leu Glu Arg Arg Trp 390         400         410         420         430
                    *           *           *           *           *
            GAG AGC CTG GTG GCG CTC TCG TTG GCG CGC CTG CCG GTG GCA GCG CAG
            Glu Ser Leu Val Ala Leu Ser Leu Ala Arg Leu Pro Val Ala Ala Gln 440         450         460         470
                        *           *           *           *
            CCC AAG GAG GCG GCC GTC CAG AGC GGC GCC GGC GAC TAC CTG CTG GGC
            Pro Lys Glu Ala Ala Val Gln Ser Gly Ala Gly Asp Tyr Leu Leu Gly 480         490         500         510         520
            *           *           *           *           *
            ATC AAG CGG CTG CGG CGG CTC TAC TGC AAC GTG GGC ATC GGC TTC CAC
            Ile Lys Arg Leu Arg Arg Leu Tyr Cys Asn Val Gly Ile Gly Phe His 530         540         550         560         570
            *           *           *           *           *
            CTC CAG GCG CTC CCC GAC GGC CGC ATC GGC GGC GCG CAC GCG GAC ACC
            Leu Gln Ala Leu Pro Asp Gly Arg Ile Gly Gly Ala His Ala Asp Thr 580         590         600         610         620
                *           *           *           *           *
            CGC GAC AGC CTG CTG GAG CTC TCG CCC GTG GAG CGG GGC GTG GTG AGC
            Arg Asp Ser Leu Leu Glu Leu Ser Pro Val Glu Arg Gly Val Val Ser
```

-continued

```
              630           640           650           660           670
               *             *             *             *             *
ATC TTC GGC GTG GCC AGC CGG TTC TTC GTG GCC ATG AGC AGC AAG GGC
Ile Phe Gly Val Ala Ser Arg Phe Phe Val Ala Met Ser Ser Lys Gly 680           690           700           710
                     *             *             *             *
AAG CTC TAT GGC TCG CCC TTC TTC ACC GAT GAG TGC ACG TTC AAG GAG
Lys Leu Tyr Gly Ser Pro Phe Phe Thr Asp Glu Cys Thr Phe Lys Glu 720           730           740           750           760
   *             *             *             *             *
ATT CTC CTT CCC AAC AAC TAC AAC GCC TAC GAG TCC TAC AAG TAC CCC
Ile Leu Leu Pro Asn Asn Tyr Asn Ala Tyr Glu Ser Tyr Lys Tyr Pro 770           780           790           800           810
   *             *             *             *             *
GGC ATG TTC ATC GCC CTG AGC AAG AAT GGG AAG ACC AAG AAG GGG AAC
Gly Met Phe Ile Ala Leu Ser Lys Asn Gly Lys Thr Lys Lys Gly Asn 820           830           840           850           860
         *             *             *             *             *
CGA GTG TCG CCC ACC ATG AAG GTC ACC CAC TTC CTC CCC AGG CTG TGA
Arg Val Ser Pro Thr Met Lys Val Thr His Phe Leu Pro Arg Leu ---

870           880           890           900           910
               *             *             *             *             *
CCC TCC AGA GGA CCC TTG CCT CAG CCT CGG GAA GCC CCT GGG AGG GCA 920           930           940           950
                     *             *             *             *
GTG CGA GGG TCA CCT TGG TGC ACT TTC TTC GGA TGA AGA GTT TAA TGC 960           970           980           990          1000
  *             *             *             *             *
AAG AGT AGG TGT AAG ATA TTT AAA TTA ATT ATT#TAA ATG TGT ATA TAT 1010          1020          1030          1040          1050
  *             *             *             *             *
TGC CAC CAA ATT ATT TAT AGT TCT GCG GGT GTG TTT TTT AAT TTT CTG 1060          1070          1080          1090          1100
         *             *             *             *             *
GGG GGA AAA AAA GAC AAA ACA AAA AAC CAA CTC TGA CTT TTC TGG TGC 1110          1120          1130          1140
               *             *             *             *
AAC AGT GGA GAA TCT TAC CAT TGG ATT TCT TTA ACT TGT--
```

---

What is claimed is:

1. An isolated DNA comprising the nucleotide sequence SEQ. ID. NO. 9.

2. The isolated DNA of claim 1 wherein said DNA is purified.

3. The DNA of claim 1 wherein said DNA further comprises a vector.

4. A procaryotic or eukaryotic host cell transformed or transfected with the DNA according to claim 1.

5. A transformed or transfected COS cell according to claim 1.

6. A transformed or transfected NIH3T3 cell according to claim 1.

7. A transformed or transfected *E. coli* cell according to claim 4.

8. The isolated DNA of claim 1 consisting of the nucleotide sequence of SEQ ID NO:9.

9. An isolated DNA comprising the nucleotide sequence SEQ ID NO: 10.

10. The DNA of claim 9 wherein said DNA is purified.

11. The DNA of claim 9 wherein said DNA further comprises a vector.

12. A procaryotic or eukaryotic host cell transformed or transfected with the DNA according to claim 9.

13. A transformed or transfected COS cell according to claim 12.

14. A transformed or transfected NIH3T3 cell according to claim 12.

15. A transformed or transfected *E. coli* cell according to claim 12.

16. The isolated DNA of claim 9 consisting of the nucleotide sequence of SEQ ID NO:10.

17. A DNA comprising a continuous coding sequence encoding a mammalian growth factor polypeptide comprising the amino acid sequence of SEQ ID NO:12.

18. The DNA of claim 17, wherein the continuous coding sequence comprises the sequence of SEQ ID NO:9.

19. A DNA comprising a continuous coding sequence encoding a mammalian growth factor polypeptide comprising the amino acid sequence of SEQ ID NO:13.

20. The DNA of claim 19, wherein the continuous coding sequence comprises the sequence of SEQ ID NO:10.

21. A DNA comprising a continuous coding sequence encoding a mammalian growth factor polypeptide comprising the amino acid sequence of SEQ ID NO:14.

* * * * *

UNITED STATES PATENT AND TRADEMARK OFFICE
CERTIFICATE OF CORRECTION

PATENT NO. : 6,432,702 B1 Page 1 of 1
APPLICATION NO. : 08/478486
DATED : August 13, 2002
INVENTOR(S) : Claudio Basilico et al.

It is certified that error appears in the above-identified patent and that said Letters Patent is hereby corrected as shown below:

On the Title page, Item (75) under Inventors, please add:

Daniela Talarico, Milano (IT)

Signed and Sealed this

Twenty-ninth Day of June, 2010

David J. Kappos
*Director of the United States Patent and Trademark Office*